(12) United States Patent
Werblin

(10) Patent No.: US 8,066,769 B2
(45) Date of Patent: Nov. 29, 2011

(54) INTRAOCULAR LENS SYSTEM

(75) Inventor: Theodore P. Werblin, Princeton, WV (US)

(73) Assignee: Werblin Research & Development Corp., Princeton, WV (US)

( * ) Notice: Subject to any disclaimer, the term of this patent is extended or adjusted under 35 U.S.C. 154(b) by 82 days.

(21) Appl. No.: 12/499,613

(22) Filed: Jul. 8, 2009

(65) Prior Publication Data

US 2010/0016964 A1 Jan. 21, 2010

Related U.S. Application Data

(63) Continuation-in-part of application No. 12/000,364, filed on Dec. 12, 2007, now Pat. No. 7,811,320, which is a continuation-in-part of application No. 11/698,875, filed on Jan. 29, 2007.

(51) Int. Cl.
*A61F 2/16* (2006.01)
(52) U.S. Cl. ............... 623/6.34; 623/6.32; 623/6.43; 623/6.38
(58) Field of Classification Search ............ 623/6.13, 623/6.32, 6.34, 6.44, 6.47
See application file for complete search history.

(56) References Cited

U.S. PATENT DOCUMENTS

| 2,036,379 | A | 4/1936 | Woodard |
| 2,039,144 | A | 4/1936 | Burgess |
| 2,168,925 | A | 8/1939 | Hewes et al. |
| 2,354,586 | A | 7/1944 | Fischer |
| 2,798,373 | A | 7/1957 | Harza |
| 2,806,809 | A | 9/1957 | Schuh |
| 3,128,576 | A | 4/1964 | Bradley |
| 3,194,130 | A | 7/1965 | Guntert |
| 3,200,482 | A | 8/1965 | Brown |
| 3,265,556 | A | 8/1966 | Hungerford et al. |
| 3,269,282 | A | 8/1966 | Beesley et al. |
| 3,458,870 | A | 8/1969 | Stone, Jr. |
| 3,945,054 | A | 3/1976 | Fedorov et al. |
| 4,010,496 | A | 3/1977 | Neefe |
| 4,240,163 | A | 12/1980 | Galin |
| 4,373,218 | A | 2/1983 | Schachar |

(Continued)

FOREIGN PATENT DOCUMENTS

DE 3428895 A1 2/1986

(Continued)

OTHER PUBLICATIONS

Wikipedia, "Presbyopia", The Free Encyclopedia, pp. 1-4, Oct. 30, 2006.

(Continued)

*Primary Examiner* — David H Willse
*Assistant Examiner* — Tiffany Shipmon
(74) *Attorney, Agent, or Firm* — Arent Fox, LLP

(57) ABSTRACT

The present invention discloses a multi-component intraocular lens implanted in an optical system of a human eye, including one or more foldable removable components, each component being foldable. One component acts as a base lens, including a flange with a slot. Another component acts is an optical assembly that may include a top lens joined to or integrated with a mid lens. The top lens, the mid lens or the optical assembly may include at least one projection that engages the slot of the base lens. The top and mid lenses are manufactured from a material having adhesive properties, wherein the top and mid lenses adhere to each other free of any material or substance being present therebetween.

28 Claims, 23 Drawing Sheets

U.S. PATENT DOCUMENTS

| | | | |
|---|---|---|---|
| 4,402,579 A | | 9/1983 | Poler |
| 4,575,373 A | | 3/1986 | Johnson |
| 4,585,456 A | | 4/1986 | Blackmore |
| 4,585,457 A | | 4/1986 | Kalb |
| 4,636,212 A | | 1/1987 | Posin et al. |
| 4,655,770 A | | 4/1987 | Gupta et al. |
| 4,685,921 A | | 8/1987 | Peyman |
| 4,685,922 A | | 8/1987 | Peyman |
| 4,731,078 A | | 3/1988 | Stoy et al. |
| 4,769,035 A | | 9/1988 | Kelman |
| 4,778,463 A | | 10/1988 | Hetland |
| 4,787,903 A | | 11/1988 | Grendahl |
| 4,834,754 A | | 5/1989 | Shearing |
| 4,838,266 A | | 6/1989 | Koziol et al. |
| 4,842,601 A | | 6/1989 | Smith |
| 4,863,466 A | | 9/1989 | Schlegel |
| 4,892,543 A | | 1/1990 | Turley |
| 4,932,971 A | | 6/1990 | Kelman |
| 4,950,289 A | | 8/1990 | Krasner |
| 5,066,301 A | | 11/1991 | Wiley |
| 5,085,013 A | * | 2/1992 | Ascosi et al. ............ 451/460 |
| 5,098,444 A | | 3/1992 | Feaster |
| 5,133,748 A | | 7/1992 | Feaster |
| 5,171,267 A | | 12/1992 | Ratner et al. |
| 5,196,027 A | | 3/1993 | Thompson et al. |
| 5,201,762 A | * | 4/1993 | Hauber ............ 623/6.34 |
| 5,222,981 A | | 6/1993 | Werblin |
| 5,288,293 A | | 2/1994 | O'Donnell, Jr. |
| 5,366,502 A | | 11/1994 | Patel |
| 5,628,798 A | | 5/1997 | Eggleston et al. |
| 5,728,155 A | | 3/1998 | Anello et al. |
| 5,777,719 A | | 7/1998 | Williams et al. |
| 5,892,617 A | | 4/1999 | Wallace |
| 5,943,117 A | | 8/1999 | Van de Velde |
| 5,968,094 A | * | 10/1999 | Werblin et al. ............ 623/6.34 |
| 6,113,633 A | | 9/2000 | Portney |
| 6,129,759 A | * | 10/2000 | Chambers ............ 623/6.17 |
| 6,254,637 B1 | | 7/2001 | Lee et al. |
| 6,255,338 B1 | | 7/2001 | Duncan et al. |
| 6,413,276 B1 | | 7/2002 | Werblin |
| 6,524,340 B2 | | 2/2003 | Israel |
| 6,551,354 B1 | | 4/2003 | Ghazizadeh et al. |
| 6,616,691 B1 | * | 9/2003 | Tran ............ 623/6.11 |
| 6,991,651 B2 | * | 1/2006 | Portney ............ 623/6.34 |
| 7,008,449 B2 | | 3/2006 | Willis et al. |
| 7,097,660 B2 | | 8/2006 | Portney |
| 7,300,464 B2 | | 11/2007 | Tran |
| 2002/0161436 A1 | | 10/2002 | Portney |
| 2003/0204254 A1 | | 10/2003 | Peng et al. |
| 2004/0117013 A1 | | 6/2004 | Schachar |
| 2005/0125058 A1 | | 6/2005 | Cumming et al. |
| 2006/0047339 A1 | * | 3/2006 | Brown ............ 623/6.13 |
| 2008/0215147 A1 | | 9/2008 | Werblin |
| 2009/0076603 A1 | | 3/2009 | Avery et al. |

FOREIGN PATENT DOCUMENTS

| | | | |
|---|---|---|---|
| EP | 0 269 198 A1 | | 6/1988 |
| EP | 0329981 | * | 8/1989 |
| EP | 0337390 | * | 10/1989 |
| EP | 0 435 525 B1 | | 7/1991 |
| FR | 2 666 735 A1 | | 3/1992 |
| WO | WO 91/06259 A1 | | 5/1991 |
| WO | WO 92/20302 A1 | | 11/1992 |

OTHER PUBLICATIONS

Ernani Serpa Junior, et al.,"Comparison of PMMA, foldable silicone and foldable acrylic hydrophobic intraocular lenses in combined phacoemulsification and trabeculectomy", Arq Bras Oftalmol, 2005; 68 (1) : 29-35.

Cyw Khng et al., "The IOL flip: rescue for foldable lens implantation gone wrong", The BMJ Interview-BJO Online Journals, Oct. 30, 2006, pp. 1-5.

Cyw Khng, et al., "The IOL flip: rescue for fordable lens implantation gone wrong", BJO Online Journals, Br. J. Ophthalmol 2003, 87, pp. 656-657 doi: 10.1136/bjo.87.5.656.

Theodore P. Werblin, "Why Should Refractive Surgeons Be Looking Beyond the Cornea?", Barraquer Lecture 1998, Journal of Refractive Surgery vol. 15 May/Jun. 1999, pp. 359-376.

Theodore P. Werblin et al,, "Epikeratophakia" The surgical correction of aphakia. III. Preliminary results of a prospective clinical trial, 99 Arch. Opth., pp. 1957-1960 (1981).

Theodore P. Werblin et al., "Hydrogel Keratophakia: Measurement of Intraocular Pressure," vol. 11, No. 4 CLAO Journal, pp. 354-357 (Oct. 1985).

Theodore P. Werblin et al.,"Refractive Corneal Surgery: The Use of Implantable Alloplastic Lens Material", 11 Austrial Journal of Opthalmology, pp. 325-331 (1983).

Theodore P. Werblin, "Lamellar Refractive Surgery: Where Have We Been and Where Are We Going?" vol. 5, No. 3, Refractive and Corneal surgery, pp. 167-176 (Jan. 1989).

Perry S. Binder et al. Hydrogel Refractive Keratoplasty. Lens Removal, and Exchanges' vol. 2, Cornea 2 at pp. 119-125.

Theodore P. Werblin et al., Epikeratophakia: The surgical correction of aphakia. II. Preliminary results in a non-human primate model; 1(3) Curr. Eye Res., pp. 131-137; 1981.

\* cited by examiner

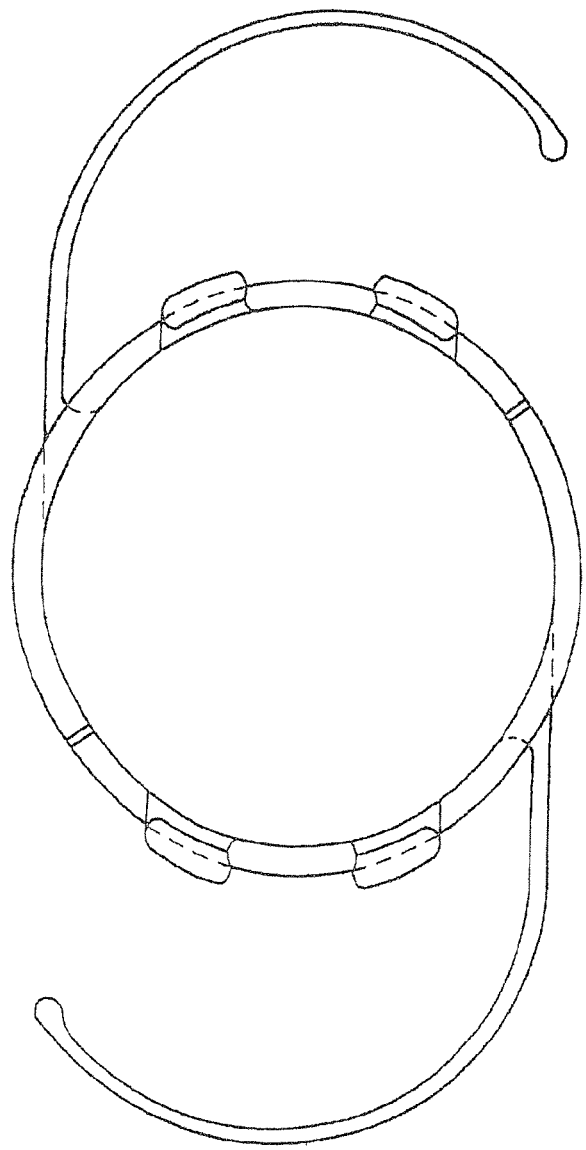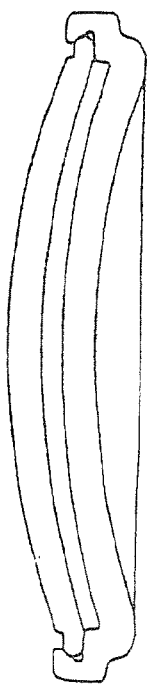
FIG.3A (RELATED ART)
FIG.3B (RELATED ART)

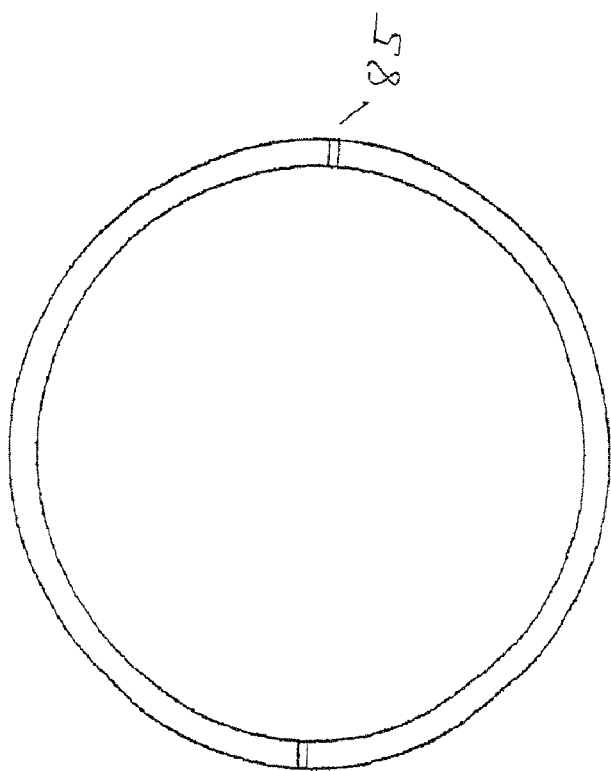
FIG.5A (RELATED ART)
FIG.5B (RELATED ART)

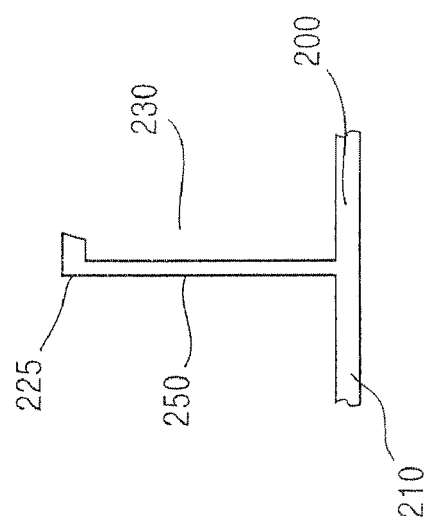
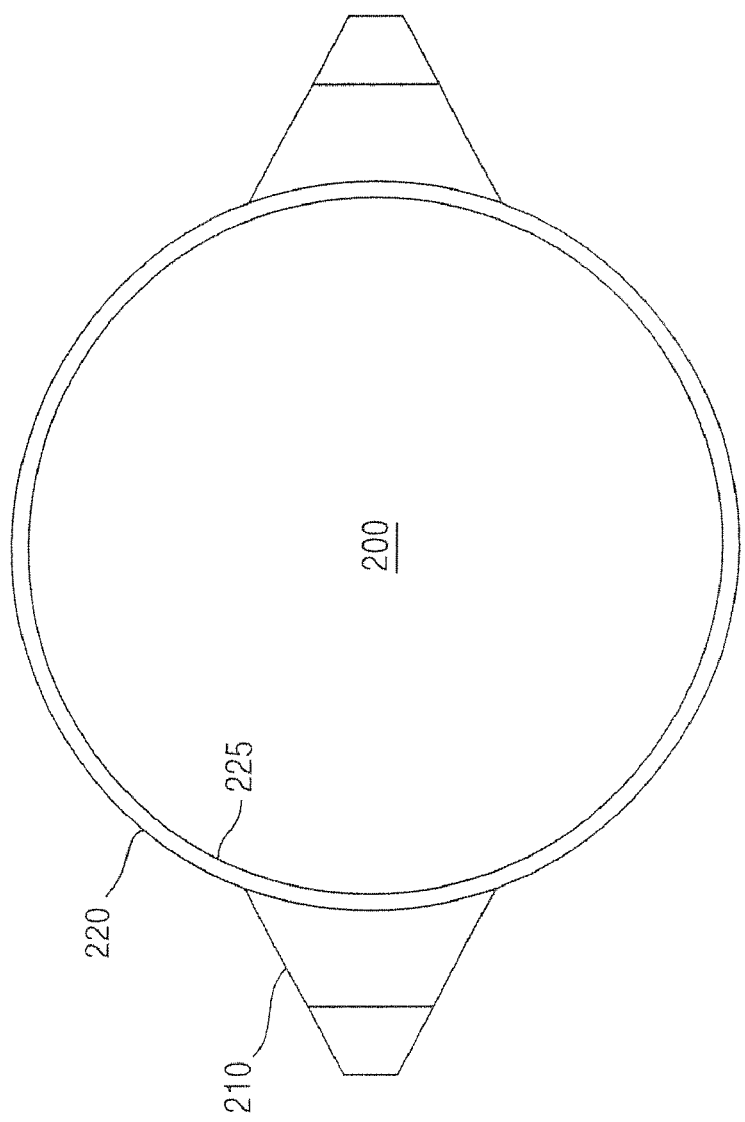
Fig. 14A (RELATED ART)
Fig. 14B (RELATED ART)

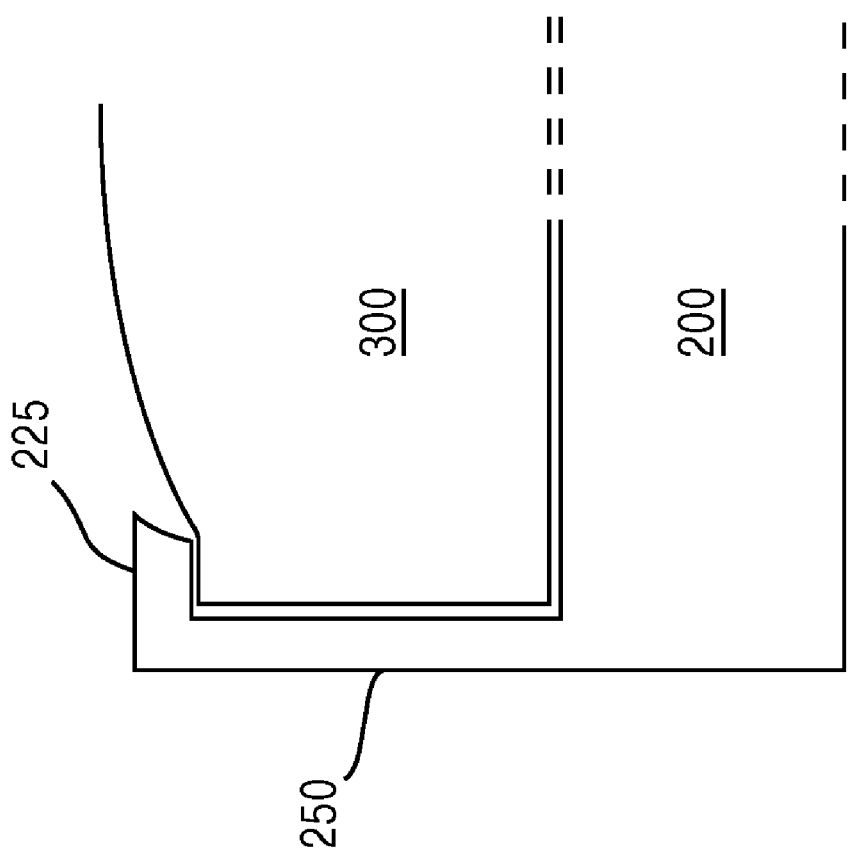

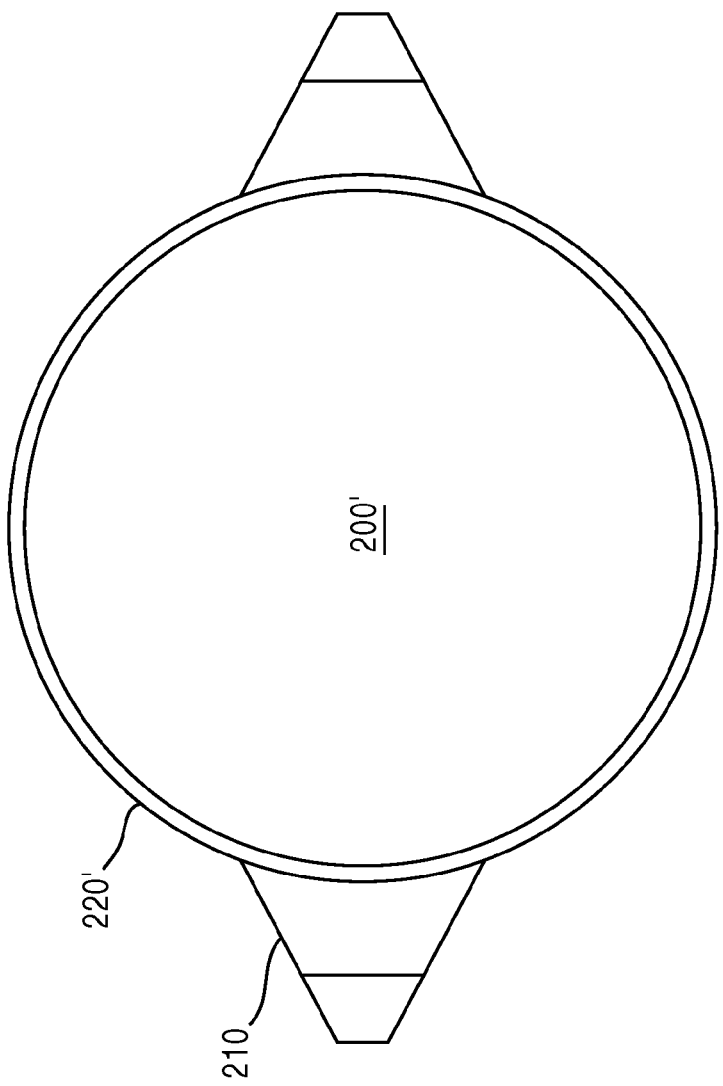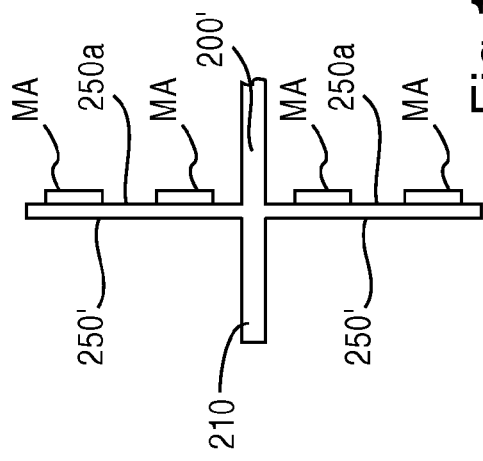
Fig.17A
Fig.17B

| 3000 |
|---|
| 2000 |
| 4000 |
| 1000 |

Fig.27A

| 2000 |
|---|
| 3000 |
| 4000 |
| 1000 |

Fig.27B

| 4000 |
|---|
| 2000 |
| 3000 |
| 1000 |

Fig.27C

| 3000 |
|---|
| 2000 |
| 4000 |
| 7000 |
| 6000 |
| 5000 |
| 1000 |

Fig.27D

| 8000 |
|---|

↓ ↓ ↓ ↓ ↓

| 1000 |
|---|

INTRAOCULAR LENS SYSTEM

CROSS-REFERENCE TO RELATED APPLICATION

This is a continuation-in-part application of application Ser. No. 12/000,364, filed Dec. 12, 2007, which is a continuation-in-part application of application Ser. No. 11/698,875, filed Jan. 29, 2007.

BACKGROUND OF THE INVENTION

1. Field of the Invention

This invention relates to a method for correcting the optical system of an eye using an intraocular lens system. Particularly, this invention relates to a method of correcting focusing abnormalities and optical aberrations measured by wave front or similar technology to quantify optical aberrations in the optical system of the eye, using a laser, or other apparatus and/or methods of fabricating or modifying a lens, for the optical system of an eye having a foldable, interchangeable intraocular lens system provided therein.

2. Description of Related Art

The field of refractive surgery has evolved rapidly during the past few decades. Current procedures and methods used by refractive surgeons may not satisfy the total refractive needs of the patient. Particularly, the most commonly performed refractive surgical procedures, such as, for example, cataract extraction with intraocular lens implantation, in addition to the most recently popularized corneal refractive surgical procedures, such as eximer laser photoblation, exhibit limitations. One reason for the limitations is the lack of post-operative refractive accuracy. The lack of post-operative refractive accuracy renders the commonly known refractive surgical procedures uncompetitive with currently available non-surgical alternatives for patients, for example, glasses and contact lenses. Further, because refractive surgery requires local or general anesthesia and incisions into the eye, a need exists for decreasing the trauma resultant from the surgery.

Recently, a need has arisen for efficient treatment of presbyopia, or the diminished power of accommodation of the eye. Presbyopia is a condition which typically affects a large number of people as they age, with the severity of the condition varying depending on the person. Difficulties arise in treating presbyopia because typically once a person manifests symptoms of presbyopia, the symptoms worsen as the person ages. As a person's condition worsens, a different, usually more powerful, lens is required to correct the condition. Conventional techniques for replacing an intraocular lens each time the patient's vision deteriorates do not always present a practical or cost-effective approach. Recent developments in the field of refractive surgery have made intraocular treatment of presbyopia a feasible course of treatment for those patients that desire or need improved vision, however a need exists for more precise techniques and devices for use in refractive intraocular surgery.

Patients suffering from eye trauma or other eye afflictions may have the iris or other portions of the eye distorted, destroyed, or discolored. Currently, such patients are typically prescribed cosmetic contact lenses. Cosmetic intraocular lens replacement is emerging as a viable alternative, however a need exists for more efficient intraocular lens replacement in order to minimize eye trauma and establish cosmetic intraocular lens replacement as a safe and effective alternative to cosmetic contact lenses and other non-surgical treatments. As surgical techniques become more effective, safer, and less painful, patients may choose to have elective lens replacement surgery to change the color, structure, or shape of their eyes. By providing a minimally invasive method for lens replacement as described in an embodiment herein, the surgeon is able to limit the drawbacks of the procedure.

Current procedures and methods for refractive surgery require the performing surgeon to execute the procedure with a high level of skill and experience. Currently, methods and procedures for carrying out refractive surgery involving intraocular lenses generally require direct visualization of the intraocular lens assembly within the eye. Such visualization, although not outside the scope of a surgeon skilled in the art, increases the degree of difficulty of the procedure, thus increasing the chance that a surgical error or other problem will arise in the surgical procedure, leading to unwanted complications. Thus, a need exists for intraocular lens assemblies and systems whose structures provide less complex methods of insertion into and extraction from the eye.

Currently, refractive cataract surgeons performing the most common refractive surgical procedure, i.e., routine cataract surgery, obtain refractive accuracies in a +/−0.75 to +/−1.00 diopter (D) range. However, the industry has established goals of obtaining refractive accuracies in the +/−0.25 D range. Therefore, there is a need in the industry to provide a more accurate alternative to the current procedure. Furthermore, analyses of current corneal refractive technologies indicate the presence of a significant amount of preexisting or naturally occurring post-operative, as well as preoperative, image distortion (optical aberration) or degradation, particularly under low light conditions, such as when driving at night.

Due to the practical limits of performing intraocular surgery, as well as the biological and physical behavior of the human eye during and after various types of intraocular surgery, predictability at the +/−0.25 D accuracy level with a single surgical procedure is difficult to achieve as a practical matter. Furthermore, factors such as biometry errors, variable wound healing, and capsular contraction around the intraocular lenses contribute to decreasing the likelihood of achieving the desired refractive accuracy. Accordingly, practitioners in the industry have found that an adjustable intraocular lens (IOL), hereinafter referred to as the MC-IOL (multi-component) or C-IOL (compound), following lens extraction surgery provides a plurality of desirable options for refractive surgeons and patients.

An adjustable IOL allows fine tuning of the initial refractive result by exchanging at least one of the optical elements of the lens implant. As a result, accuracies in the +/−0.25 D range are readily attainable. Furthermore, patients are provided with an opportunity to exchange the "old" lens components with new and hopefully more accurate components. Such an objective is obtainable if the surgeon has an effective, efficient, and safe method of performing lens element exchanges. Additionally, months and/or years after the refractive surgical procedure, if the optical properties of the inserted IOL, for example, the multifocality, become problematic, the surgeon should have the ability to safely exchange the undesirable optical elements of the IOL to correct any optical aberrations that the patient will not or cannot tolerate.

In 1990, the inventor of this application developed a multi-component intraocular lens, hereinafter referred to as the MC-IOL (FIG. 1), for use following clear lens or refractive cataract surgery, wherein the optical properties of the MC-IOL can be modified at any post-operative time. The base intraocular lens component of the MC-IOL is shown in FIG.

1. The mid lens attaches to the top of the base lens and holds the third component of the MC-IOL, the top lens, in place.

The base intraocular lens 10 and the mid lens 20 each have securing flanges 16, 18 and 20, 24, respectively, extending therefrom. The MC-IOL also comprises at least one top lens 30, as illustrated in FIG. 1. The top lens 30 is positioned on top of the mid lens 20. See FIGS. 1-2.

The MC-IOL also includes projections (or haptics) 11 and 13 which securely hold the MC-IOL in the tissue of the human eye. The above-described structure permits the base intraocular lens 10 to form a platform upon which the mid lens 20 is placed, and to hold the top lens 30. During routine cataract surgery, the MC-IOL replaces the crystalline lens of the human eye. Once a patient's eye has healed after such a surgery, the surgeon reenters the eye and replaces, if necessary, and more than once, the top lens 30 and the mid lens 20 to modify the optical characteristics of the eye until the desired levels for each optical characteristic are attained.

FIGS. 3A-3B illustrate an assembled compound intraocular lens, hereinafter C-IOL, used with a preexisting lens within the human eye. The C-IOL has two components similar to the mid lens (FIGS. 4A-4B) and the top lens (FIGS. 5A-5B) components of the MC-IOL. FIG. 5A also illustrates the axis orientation mark 85 used in some embodiments of MC-IOL lenses to aid in positioning and orienting the lens. The preexisting lens can be the crystalline lens of the eye with the C-IOL placed in the sulcus (FIG. 6) or in the anterior chamber angle (FIG. 7) of the eye's optical system. However, the C-IOL can also be used with a conventional IOL, as well as with an accommodating IOL, and mounted in the sulcus (FIG. 8), in the anterior chamber angle (FIG. 9), in the anterior chamber with posterior chamber fixation (FIG. 10) or in the anterior chamber with iris fixation (FIG. 11). Thus, a surgeon modifies the optical characteristics of the optical system of the eye by using the mid and top lenses in tandem with the preexisting conventional IOL implant or crystalline lens of the eye.

The C-IOL and MC-IOL provide numerous enhanced features. For example, the C-IOL and MC-IOL can each be structured as a monofocal or multifocal optical system, correct astigmatism, as well as comprise ultraviolet light-absorbing, tinted, or other such chemically treated materials.

It should be understood that there are various reasons why an adjustable MC-IOL or C-IOL is more desirable than a single component implant. In order to achieve all the permutations and combinations of the astigmatism, multifocality, and spherical correction needed to achieve emmetropia would take an inventory of over ten thousand lenses, whereas with the MC-IOL (multiple components) concept, an inventory of about one hundred components would be necessary. With anterior chamber lenses, progressive encapsulation or engulfment of the lens haptics by uveal tissue in the angle often occurs 1-2 years post-operatively. The engulfment typically makes the removal of the lenses and their haptics more difficult. Exchange of iris fixated anterior chamber lenses does not typically guarantee precise position or orientation. Posterior chamber lenses similarly cannot be removed because of posterior capsule fibrosis. Easy removal and exchangeability is critical for any customized emmetropic system, which can be provided by a specially designed multicomponent lens system.

Therefore, based on the above, a MC-IOL having three elements rather than one permits refractive customization and adjustability for all refractive errors, as well as for all patients, while using a minimal number of lens elements or parts and requiring little customization on the part of the manufacturer. Thus, it has become very important in the refractive surgery art to be able to individualize and/or customize surgery such that the surgeon can easily and safely, as well as accurately, modify the refractive power of an intraocular lens implant.

For example, U.S. Pat. No. 5,288,293 to O'Donnell, Jr. discloses a method of modifying a single IOL. O'Donnell suggests that the refractive power of a single IOL may be varied before implantation so that the changes can be made in situ by the ophthalmologist after determining the extent of correction required to improve the vision of the patient before the lens is made. However, the surgical implantation procedure itself may create additional optical aberrations which cannot be anticipated preoperatively and thus the primary lens implant cannot account for these optical aberrations.

As such, it may be argued that if a lens can be modified before being implanted, as suggested by O'Donnell, Jr., it should be possible to modify the implanted lens by removing the implanted lens, modifying the lens, and then reimplanting the modified lens into the optical system of the eye. However, the design of current intraocular lenses typically makes such a procedure difficult and impractical. Furthermore, after a period of time with normal healing, it becomes physically dangerous and/or nearly impossible to the patient to have the implanted lens removed once the eye tissue takes hold on the capsular fixation holes of the lens. Therefore, such an argument is not realistic, practical, or safe. A single component intraocular lens, which in general is not designed to be removed and with only two optical surfaces, cannot accurately allow for compensation of sphere, cylinder, cylindrical axis, and all forms of optical aberrations that may be discovered after the initial implantation. However, the MC-IOL typically will have four removable optical surfaces which can compensate for these optical properties.

The inventor of this application invented the previously discussed MC-IOL and C-IOL that are designed specifically to permit the easy exchange of optical elements at a postoperative period without risk to the human eye or to the patient, beyond the risk of ordinary intraocular surgery. The easy exchangeability of optical elements is critical because the actual surgery of implanting the lens in the first place, as well as variances in the manner in which the eye heals after implantation, potentially create distortions which may not stabilize for several months after the operation. Therefore, the ability to measure and to compensate for the distortion(s) optimally takes place several months after surgery and cannot typically be predicted prior thereto. Since the same surgical wound is used for both the primary and secondary operations, additional distortion due to wound healing would not be anticipated as a result of the second operation.

Furthermore, the ability to exchange optical elements of a multicomponent or compound intraocular lens can be economical compared to removing, modifying, and re-implanting a single component lens, as well as easier to perform.

The MC-IOL has four surfaces available for modification, two plano and two convex. Preferably, the modification is made only to the plano surfaces to avoid interfering with the convex side which may already be used for correction of astigmatism (cylinder) or used as a multifocal lens surface. The same preference applies to the CIOL, which has two surfaces available for modification, one plano and the other convex.

The inventor of this application also developed a system for correcting optical aberrations in the MC-IOL, as described, for example, in U.S. Pat. No. 6,413,276, for conducting measurements to determine any residual or new aberrations present in an operated eye after the biological healing parameters have stabilized, as well as to correct any errors in sphere, cylinder, or cylindrical axis, and for modifying one, two, or more existing lens elements within the implanted optical system based on the conducted measurements.

In conventional multi-component intraocular lens designs, the surgical procedure required to implant the intraocular lens components requires a high level of surgeon skill. For example, implantation of the removable component of the lens requires the surgeon to directly visualize the placement of the lens in order to match the notches with the flanges. Further, removal of the removable lens component requires a special forceps tool for grabbing the base lens, and releasing the tabs holding the sandwich and cap lens together with the base lens (see, for example, the system described in U.S. Pat. No. 5,968,094).

Historically intraocular lens systems used a rigid one piece poly methyl methacrylate (PMMA) lens. The PMMA lens is approximately six millimeters in diameter. Because the PMMA lens is rigid, insertion of the PMMA intraocular lens generally requires a seven or eight millimeter incision to be inserted into the eye. In contrast, a flexible or foldable lens can be manipulated and compacted to a much smaller size. Once compacted, the multi-component intraocular lens can be delivered using a relatively smaller incision, for example, about three millimeters or less. By using a smaller incision, the patient reaps optical and practical benefits. From an optical standpoint, any time incisions are made to the cornea, the cornea loses some of its natural globularity due to imperfections caused by the incisions and the resultant trauma. The imperfections in the cornea lead to induced astigmatism, or optical aberrations caused by irregularities in the shape of the cornea. By minimizing the size of the corneal incision, a surgeon may also minimize the amount of induced astigmatism. Even though the three-component design simplifies the process of correcting induced astigmatism, minimizing the amount of induced astigmatism remains a primary goal for all intraocular surgeries.

As a practical matter, by making a smaller incision, the surgeon reduces the amount of actual trauma to the eye, thus reducing the occurrence of complications and decreasing the time for recovery. These advantages are further realized if the surgeon is able to perform the intraocular surgery using an incision small enough to heal without the use of stitches, wherein the incision is small enough to allow the eye's natural ocular pressure to hold the incision together during the healing process.

The inventor's application Ser. No. 11/698,875 overcame the above-described drawbacks of the related art. FIGS. 12-16 illustrate the invention disclosed in the '875 patent application.

For example, FIG. 12A shows a top or plan view of an intraocular foldable base lens 100, which is similar to the MC-IOL base lens illustrated in FIG. 3. The base lens 100 attaches to the eye by at least one haptic 120 and while the base lens 100 in FIG. 12A can be secured to the eye by at least one haptic, it is preferable that at least two haptics 120 be used. As shown in FIG. 12A, each haptic 120 extends outward from the base lens 100, and is tilted from between 10 to 20 degrees, in either direction, relative to a plane taken across the base lens, preferably having a 15 degree positive tilt.

As shown in FIG. 12B, as well as later in FIG. 24, the base lens 100 (1000, FIG. 24) can also include one or more flanges 105 (1005, FIG. 24) disposed on and extending outwardly away from the body of the base lens 100 (1000, FIG. 24). Each flange 105 (1005, FIG. 24) can also have a slot 110 (1100, FIG. 24) designed or configured to receive or accept an assembly of a top lens 300 (3000, FIG. 24) and a mid lens 200 (2000, FIG. 24) therein. Each flange 105 (1005, FIG. 24) and slot 110 (1100, FIG. 24) is an essential feature to the design of base lens 100 (1000, FIG. 24). The MC-IOL concept allows for adjustments or enhancement operations, beyond its use in primary cataract, clear lens, surgery to compensate for any miscalculation or any biological variability or any change in the condition of the eye over time after the primary operation. In order for these surgical adjustments to be workable, the surgeon must have easy access to the front lens assembly 200, 300 (2000, 3000 FIG. 24). To assure this, the front lens assembly 200, 300 (2000, 3000 FIG. 24) must be left out of the capsule, in the sulcus. On the other hand, the base lens 100 (1000, FIG. 24) is left in the capsule. In the primary surgery after the MC-IOL is inserted and the edges of the capsule are placed between the haptics 210, see FIG. 14A (2100, FIG. 24) of the front lens assembly 200, 300 (2000, 3000 FIG. 24) and the base lens 100 (1000, FIG. 24), the vertically extending flanges 105 (1005, FIG. 24) and their corresponding slots 110 (1100, FIG. 24) allow a space between the haptics 210, see FIG. 14A (2100, FIG. 24) of the front lens assembly 200, 300 (2000, 3000 FIG. 24) and the base lens 100 (1000, FIG. 24) so that a special instrument, referred to as a capsule snare, allows the surgeon to place the front lens assembly haptic 210 (2100, FIG. 24) above the edges of the capsule (6-7 mm capsulorrhexis necessary in the primary surgery) thus capturing the capsule between the haptics 210 and 120 (2100 and 1200 of FIG. 24). The remaining capsule "cellophane wraps" around the edges, the haptics 120 (1200, FIG. 24) and the edges of the base lens 100 (1000, FIG. 24) during the healing process after the cataract, clear lens, surgery. The "cellophane wrapping" makes it extremely difficult and dangerous for the surgeon to gain access to any surface of the base lens 100 (1000, FIG. 24) after the primary surgery heals, which is necessary for enhancement operations. The vertically extending flanges 105 (1005, FIG. 24) and corresponding slots 110 (1100, FIG. 24) position the front lens assembly 200, 300 (2000, 3000, FIG. 24) in front of or away from the "cellophane wrapped" posterior capsule, that is, in the sulcus, making surgical removal and replacement of the front lens assembly 200, 300 (2000, 3000, FIG. 24), very safe and technically simple.

Put another way, the flanges 105 (1005, FIG. 24) and slots 110 (1100, FIG. 24) are necessary features of the MC-IOL design to assure easy removal and replacement of the front lens assembly 200, 300 (2000, 3000, FIG. 24) during an enhancement operation. Without the vertical flange 105 (1005, FIG. 24), the edges and haptics 210 (2100, FIG. 24) are inaccessible to the surgeon due to capsule contracture around the edges and haptics 120 (1200, FIG. 24) of the base lens 100 (1000, FIG. 24), that is, the normal healing process. The structural configuration of the flange 105 (1005, FIG. 24) and corresponding slot 110 (1100, FIG. 24) position the base lens assembly 200, 300 (2000, 3000, FIG. 24) in front of the capsule, in the sulcus, which allows or facilitates easy access for the surgeon to remove and the replace the front lens assembly 200, 300 (2000, 3000, FIG. 24) during an enhancement operation any time during the life of the patient after the primary operation has healed.

The base lens in FIG. 13 is similar to the base lens 100 (FIGS. 12A-12B), except for a groove 130 being defined therein that extends along the entire outer periphery, and a plurality of attachment points 140, which serve to attach the optical region 150 to the base lens.

The foldable MC-IOL disclosed in the inventor's '875 application includes two or more additional refractive components, i.e., a top lens 300 and a mid lens 200. The mid lens 200, which typically allows spherical adjustments, is illustrated in FIGS. 14A-14B, while the top lens 300 (FIG. 15) carries the astigmatic correction and has an orientation projection 305. The mid lens 200 may include at least one projection 210 extending away from the body of the mid lens 200 and may have varying lengths depending on the shape and number of projections. The mid lens 200 also includes a side portion 250 which extends upward, and terminates at a lip 225, as illustrated in FIG. 14B. The side portion 250 and lip 225 extend along the outer circumference of the mid lens 200, thereby defining a notch 230.

Prior to insertion into the eye, the top lens 300 engages the notch 225 of the mid lens, such that a seal is formed between the notch 225 and the top lens 300, and which holds the mid lens 200 and the top lens 300 together as a single assembly (FIG. 16). The top lens 300 is oriented so that, when the top lens 300 is inserted into the mid lens 200, raised projections or notches 305 of the top lens 300 face the mid lens 200 or may also project away from the mid lens 200. The notches or projections 305 can provide directional and axial orientation for the top lens, similar to the axis orientation marks 85 of FIG. 5.

The lens manufacturer assembles the mid lens 200 and the top lens 300 to a predetermined axis orientation to correct the astigmatism, and then the surgeon, outside the eye assembles the front lens assembly 200, 300, and the base lens 100 and inserts the completed assembly into the eye as one folded piece such that the mid lens 200 is sandwiched between the base lens 100 and top lens 300. Alternatively, the surgeon inserts the top lens 300 and the mid lens 200 assembly into the eye and then attaches the assembly to the base lens 100 by sliding a projection 210 of the mid lens 200 into a slot 110 of a corresponding flange 105 of the base lens 100, the latter two step assembly allows for a smaller surgical incision. Once the first projection 210 is in place in the corresponding first slot 110, if more projections are present in the mid lens 200, then the surgeon adjusts the mid lens 200 and the top lens 300 until the other projection(s) 210 line up with the other slot(s) 105. Once all projections 210 have been inserted into their corresponding slots 110, the assembly of the top lens 300 and the mid lens 200 is secured in the base lens 100, and the procedure is completed.

In the event that the assembly formed by the mid lens 200 and the top lens 300 requires replacement, the surgeon may perform a disassembly procedure as discussed herein. First, a cannula containing visco elastic material would be introduced into the eye and positioned at the interface between the lens assembly (mid lens 200 and top lens 300) and the base lens 100. The injection of visco elastic causes the mid 200/top 300 lens assembly to elevate, thus disengaging the projections 210 from the slots 110 in the base lens 100. The original lens assembly would then be removed from the eye, and a new lens assembly placed into the eye and attached to the base lens 100 similar to as described above in the primary operation.

The inventor's application Ser. No. 12/000,364 taught a different orientation of the mid lens and top lens than the orientation disclosed in the inventor's '875 application. For example, the '364 application inverted or reversed the order of the mid lens and top lens such that the top lens is placed on top of the base lens and the mid lens then positioned on top of the top lens such that the three components are oriented in an order where the base lens is most posterior relative to the patient's eye. The top lens is then placed on the base lens and the mid lens arranged on the top lens such that the mid lens is most anterior relative to the patient's eye and the top lens is arranged between or in the middle of the base and mid lens.

Moreover, while the inventor's '875 application teaches the mid lens includes a notch with which a projection of the top lens engages to securely maintain the mid/top lens assembly, the inventor's '364 application joins the top and mid lenses to each other using a joining means, such as, for example, a medical adhesive that is applied in at least one location where the mid lens interfaces with the top lens.

Further, the inventor's '364 application teaches a feature wherein the haptic of the mid lens has projections extending anteriorly and posteriorly that capture the top lens (circular configuration) and retain the top and mid lens (circular configuration) as an optical assembly.

As shown in FIGS. 17A-21, the inventor's '364 application discloses a medical adhesive MA is used to join the mid lens 200' and top lens 300', respectively, together as a single, integrated unit or assembly. For example, FIGS. 17B and 18 illustrate how the medical adhesive MA is applied to the inner surface 250a of a side portion 250' of the mid lens 200' and/or an outer peripheral surface 350a of the top lens 300' to securely retain the mid lens 200' and top lens 300' together. Alternatively, as shown in FIGS. 19-21, the inventor's '364 application teaches that the medical adhesive MA can also be applied along an upper surface of the mid lens 200'' and/or an entire lower surface of the top lens 300'', either entirely or in select, discrete locations thereon, which directly opposes the upper surface of the mid lens 200'' to join the top and mid lenses 300'' and 200'' into a single unit or assembly.

SUMMARY OF THE INVENTION

It is an aspect of this invention to provide a multi-component intraocular lens system with components that are removable and replaceable after placement in the eye.

It is an additional aspect of the present invention to provide a multi-component intraocular lens system with foldable components in order to minimize trauma to the eye. Trauma is minimized by allowing the use of a delivery system for the foldable lens which requires an incision smaller than the unfolded diameter of the foldable lens.

It is a further aspect of this invention to provide a multi-component intraocular lens system with components designed to simplify the surgical procedure for intraocular lens component insertion. An embodiment of the present invention includes a multi-component intraocular lens, wherein the base lens is attached with haptics, and the top and mid lenses are assembled outside the eye.

Furthermore, the present invention omits the use of the medical adhesive MA used in the inventor's '364 application. Specifically, an embodiment of the present invention includes manufacturing the mid lens and the top lens from a material having adhesive properties such that the mid lens and the top lens naturally adhere to each other. For example, the material from which the top and mid lenses are manufactured can be, but is in no way limited to, a hydrophilic acrylic that has a self-adhesive property such that the top and mid lenses adhere together without the need for a medical adhesive or any other joining means being administered to either of the lenses.

Further, the present invention includes a feature wherein the top lens and the mid lens are manufactured from the same material. It is also within the scope of the present invention for the top lens and the mid lens to be manufactured from different materials. Additionally, the base lens may be made from the same material as either one of or both of the top lens and the mid lens, or the base lens may be made from a material that is different from the material from which the top lens and the mid lens are manufactured. For example, while an optical assembly defined by the top lens and the mid lens joined together may be made of a hydrophilic material, the base lens may be made form a non-hydrophilic material.

Moreover, to prevent the optical assembly defined by the top and mid lenses from undesirably adhering or sticking to the base lens, it is an aspect of the present invention to negate the self-adhesive property of the top and mid lenses by treating at least the non-optical aspects of at least one, and preferably both, of the top lens and the mid lens so the optical assembly does not stick or adhere to the base lens. Such treatment may include, but is in no way limited to, frosting the non-optical aspects of the optical assembly, e.g., the surface of the flange contacting the base lens, with a non-adhesive substance, or providing the portions of the optical assembly and/or the base lens that contact each other with a surface treatment wherein the surface is modified such that the optical assembly and base lens will not adhere to each other, e.g., knurled surfaces, and the like.

Further, the present invention includes a feature wherein the optical assembly is expanded to include additional lenses than the mid lens and top leans. An aspect of the present invention is to stack a plurality of lenses that make up the optical assembly, and insert the optical assembly into the base lens. The stacked optical assembly would include a plurality of lenses, each lens addressing different optical elements. For example, if the mid lens is a spherical lens and the top lens is a toric lens, another lens of the optical assembly could address or correct chromophore or color related issues, yet another lens could address astigmatisms, another lens could address nearsightedness or farsightedness, while another lens could address higher order optical aberrations or spherical aberrations or both. The additional lenses could also be stacked on either side of the mid lens, that is, either between the mid lens and the top lens, or between the mid lens and the base lens, or even on top of the top lens such that the top lens is between the mid lens and any additional lenses.

The intraocular lens system of the present invention allows assembly without the use of special equipment or techniques for securing the top and mid lenses together.

It is an aspect of the present invention to provide a modified multi-component intraocular lens implanted in an optical system of a human eye, including one or more removable components, with each component being foldable, and where two or more removable components are used, they are also connected to each other.

BRIEF DESCRIPTION OF THE FIGURES

In the drawings:

FIGS. 3A-3B are exploded views of a currently known two component compound intraocular lens;

FIGS. 5A-5B are top and side views, respectively, of a type of compound intraocular lens-top lens component;

FIGS. 14A and 14B are an exploded top view and an exploded side view, respectively, of a mid lens replaceable component of a currently known foldable multi-component intraocular lens;

FIG. 16 is a side view of a currently known optical assembly wherein a top lens is inserted into a mid lens;

FIGS. 17A and 17B are a top view and an exploded side view, respectively, of a top lens replaceable component of a currently known foldable multi-component intraocular lens;

FIGS. 27A-27D are schematic diagrams that illustrate various manners in which the lenses of the optical assembly can be arranged; and FIG. 28 is a schematic diagram of an embodiment wherein the mid lens and top lens are integrated into a single lens that is placed within the base lens.

DETAILED DESCRIPTION OF THE PREFERRED EMBODIMENTS

It should be noted that according to the preferred embodiments of the present invention, the fully assembled or end appearance of the base lens 1000 of the present invention is substantially similar to the base lens 100 and 100" described above. Therefore, a detailed description of many of the common features of the base lens 1000 relative to the base lens 100 and 100" is omitted herefrom in order to avoid redundancy.

As in the disclosure of the '875 and '364 applications, the foldable MC-IOL according to the present invention also includes one or more additional refractive components, including an assembly of a mid lens 2000 and a top lens 3000, described more fully herein. It should be noted that the top lens 300 and the mid lens 200 of the '875 application, as well as the mid lens 200' and top lens 300' of the '364 application, are similar to the mid lens 2000 and top lens 3000 described below, with the exception of certain distinguishing aspects.

Figure 1:
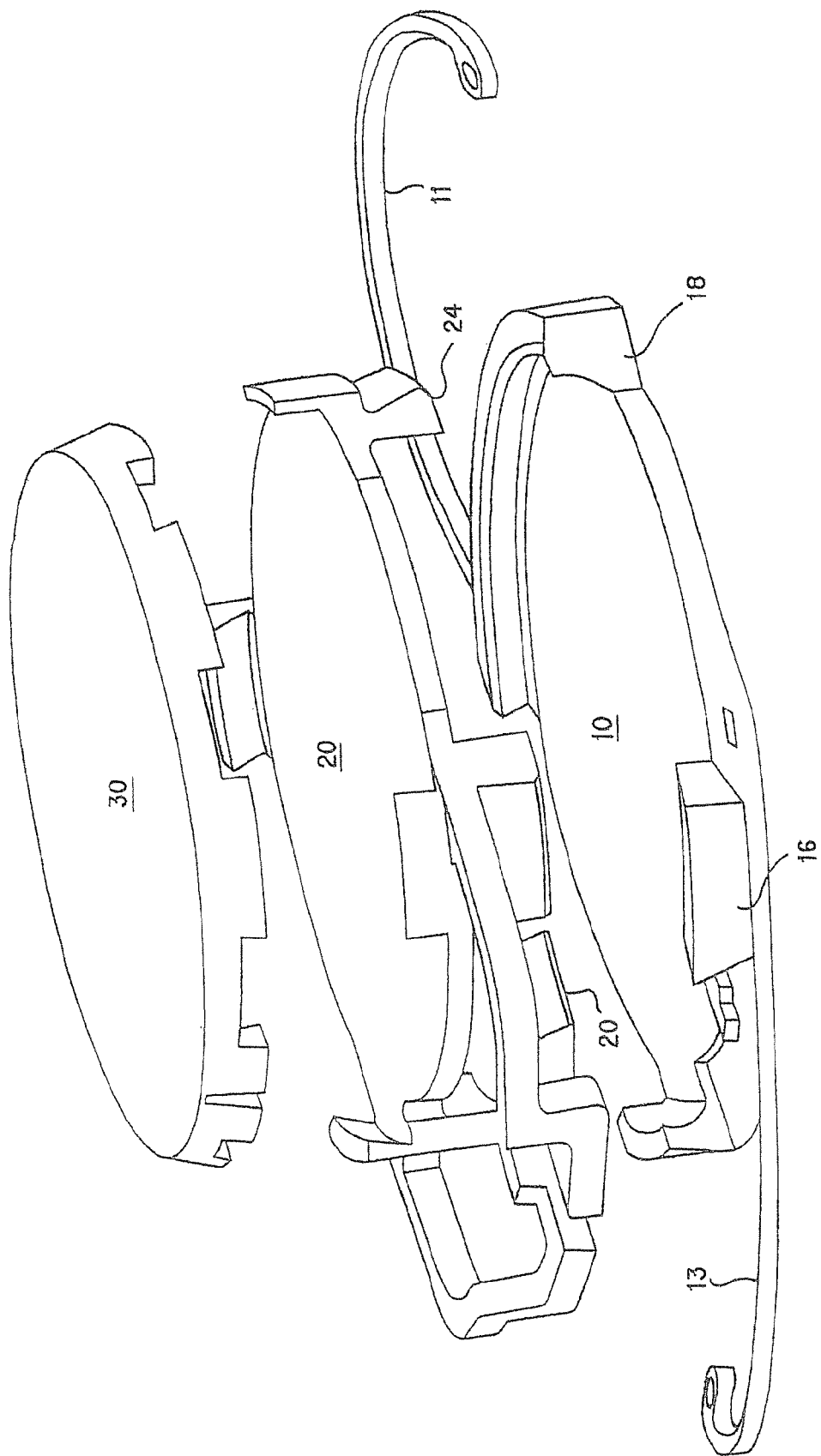
FIG. 1 is a plan view of the base, mid, and top lens components of a currently known multi-component intraocular rigid lens.
Figure 2:
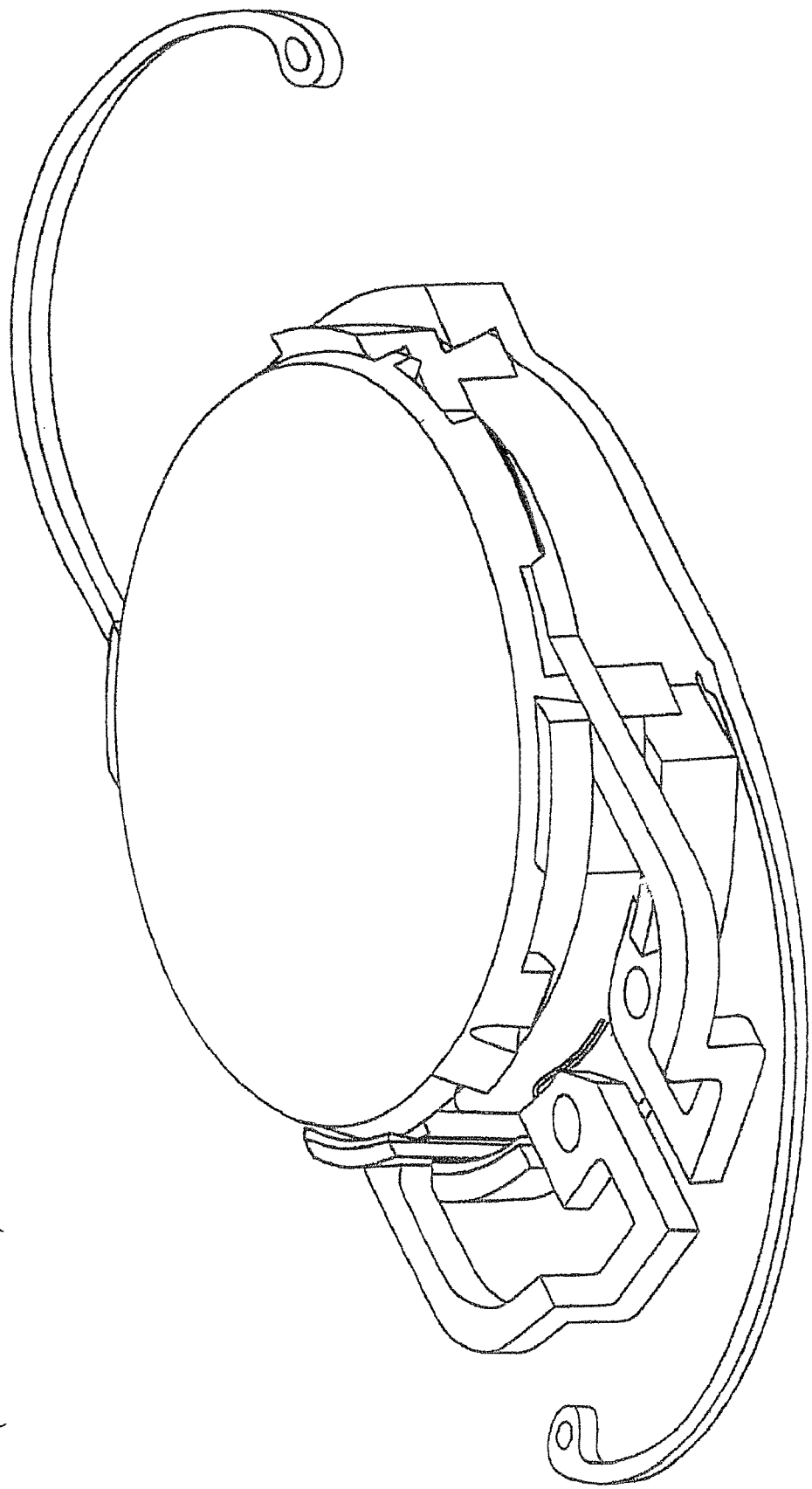
FIG. 2 is an exploded side view of the assembled base, top, and mid lenses of the currently known multi-component intraocular rigid lens shown in FIG. 1.
Figure 4A:
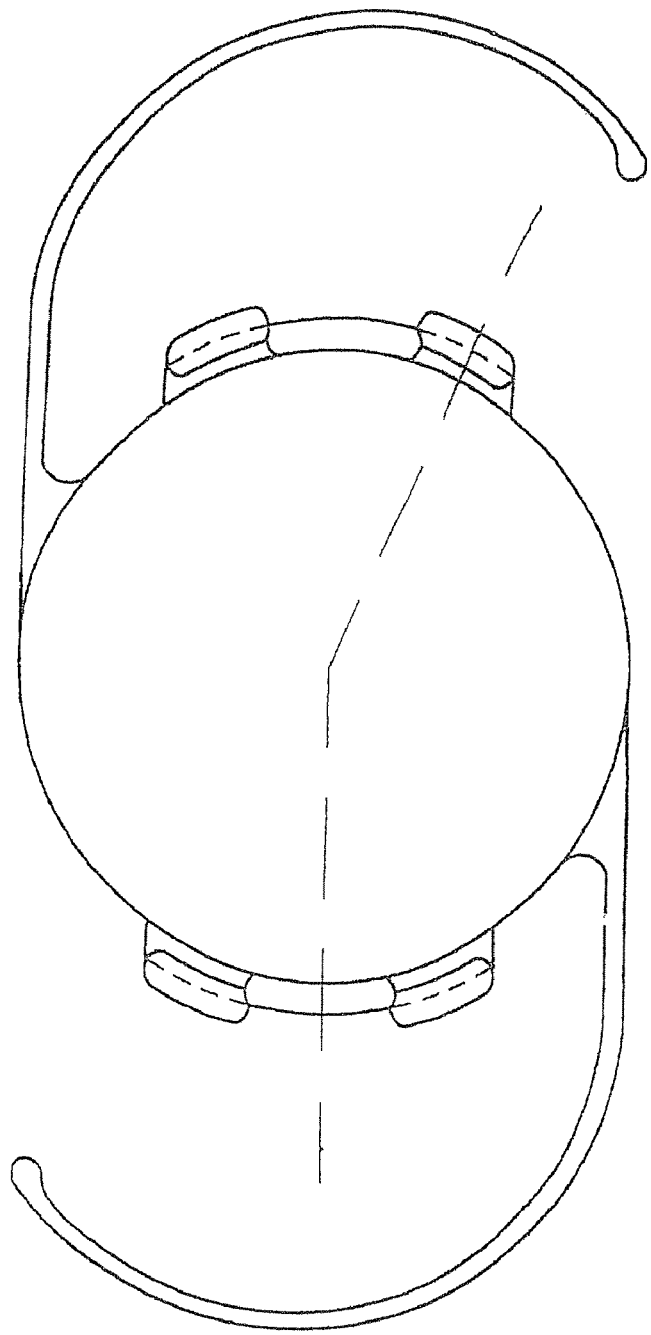
FIGS. 4A-4B are top and side views, respectively, of a type of compound intraocular lens-top lens component.
Figure 4B:
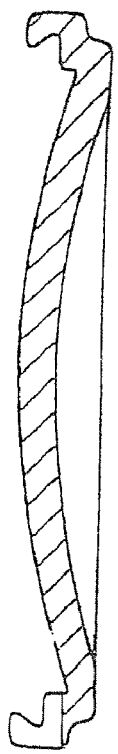
Figure 6:
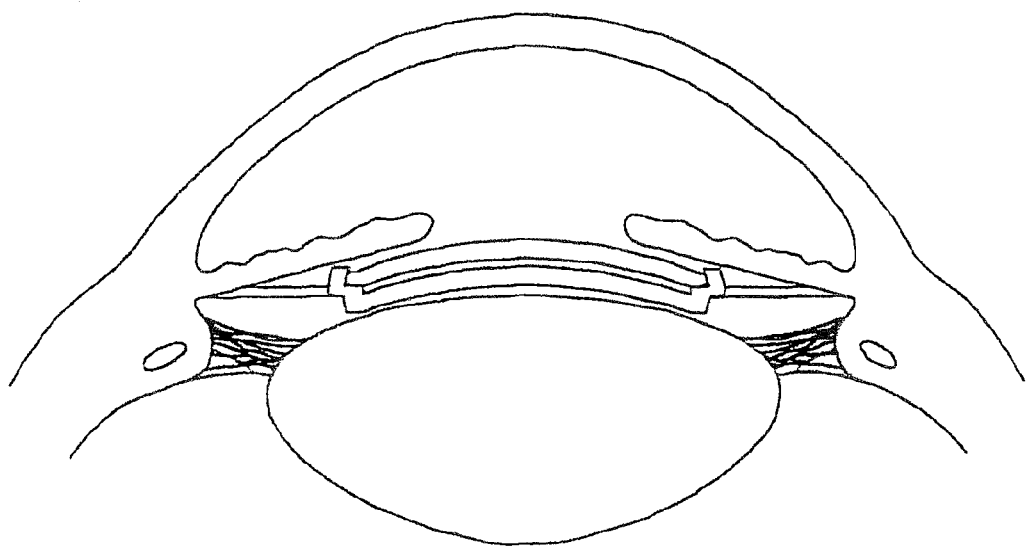
FIG. 6 is a side view of a compound intraocular lens implanted within a human eye ciliary sulcus.
Figure 7:
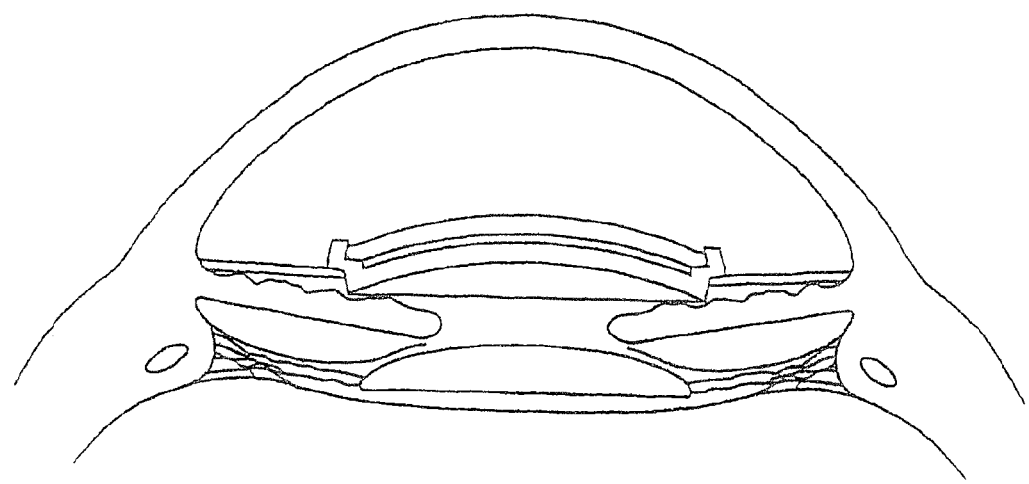
FIG. 7 is a side view of another compound intraocular lens implanted within a human eye using the anterior chamber angle as support.
Figure 8:
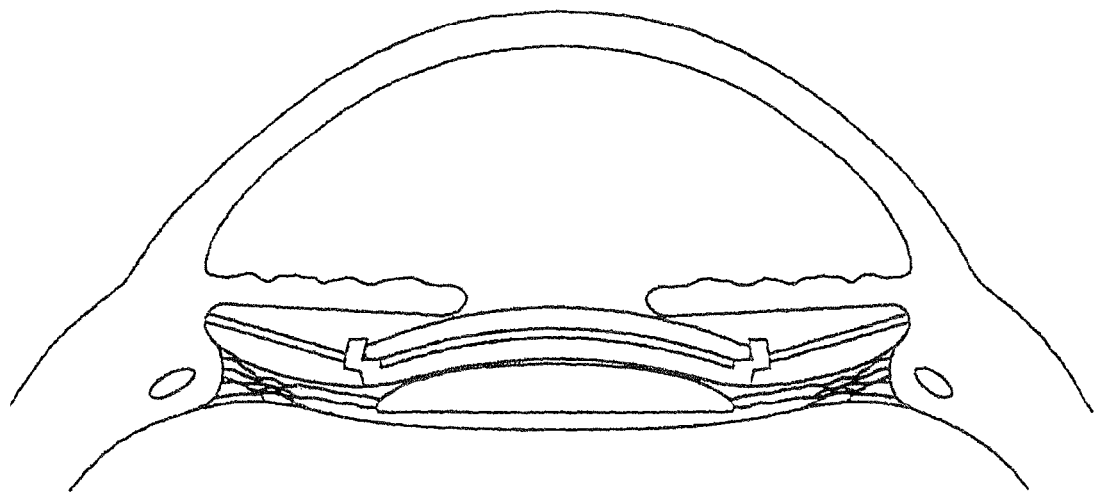
FIG. 8 is a side view of a sulcus mounted compound intraocular lens implanted within a human eye with a previously implanted single component conventional intraocular lens mounted in the capsular bag.
Figure 9:
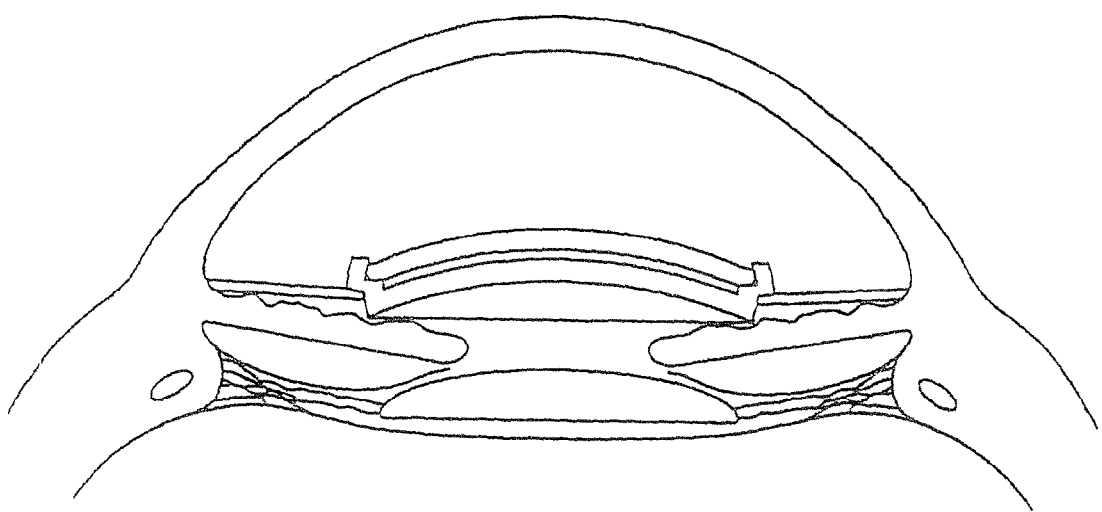
FIG. 9 is a side view of an anterior chamber mounted compound intraocular lens implanted within a human eye with a previously implanted single component conventional intraocular lens mounted in the capsular bag.
Figure 10:
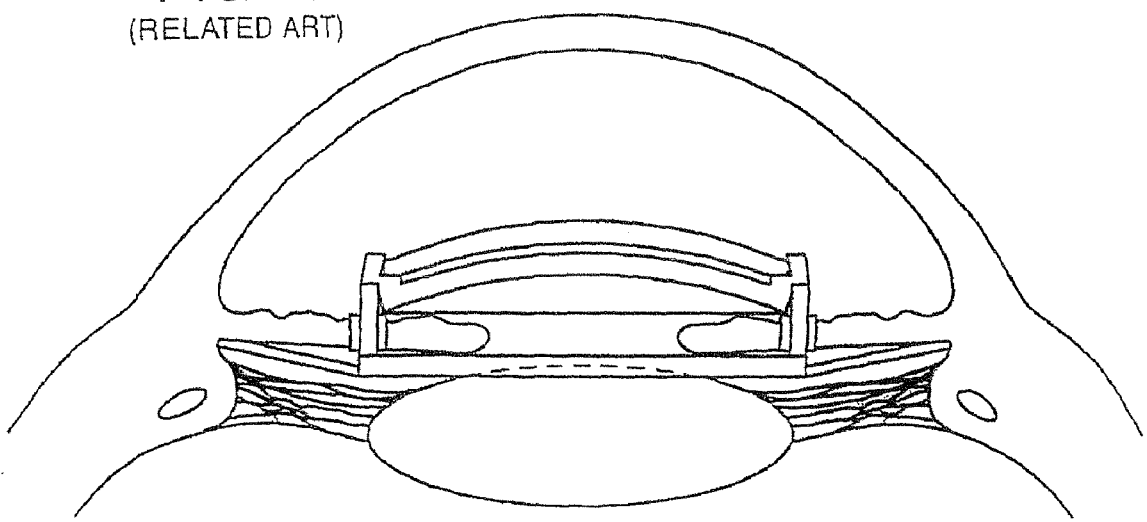
FIG. 10 is a side view of an anterior chamber mounted compound intraocular lens on a support secured in the posterior chamber and is implanted within a human eye with a previously implanted single component conventional intraocular lens mounted in the capsular bag.
Figure 11:
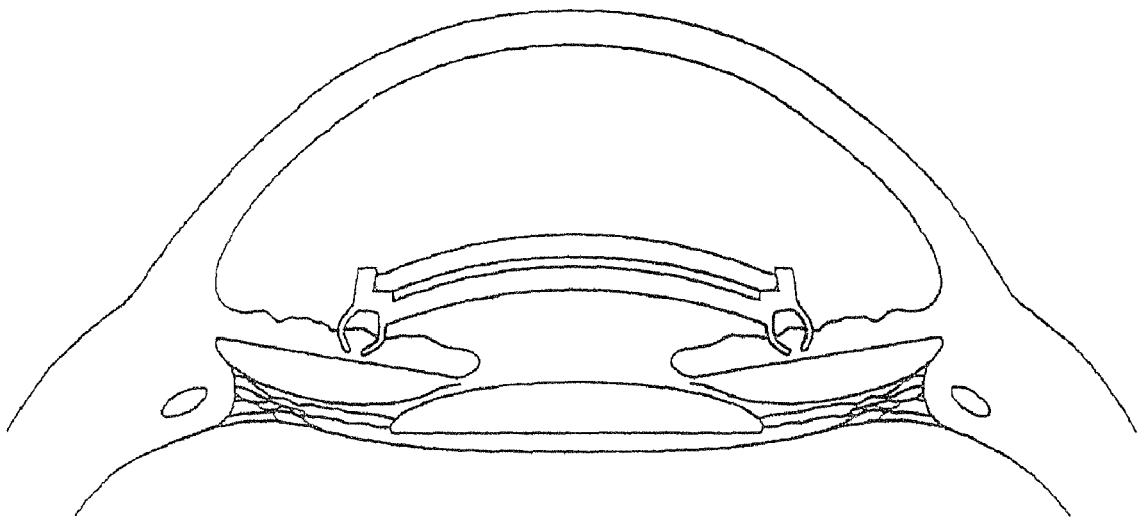
FIG. 11 is a side view of an iris fixated compound intraocular lens in the anterior chamber that is implanted within a human eye with a previously implanted single component conventional intraocular lens mounted in the capsular bag.
Figure 12B:
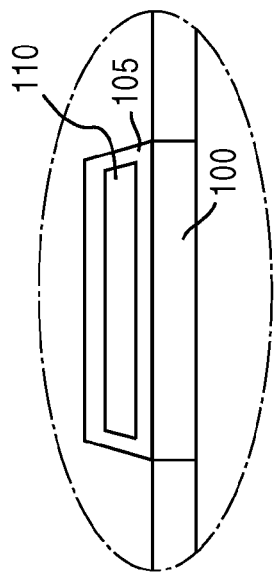
FIG. 12B is a side view of an enlarged portion of the base component shown in FIG. 12A.
Figure 12A:
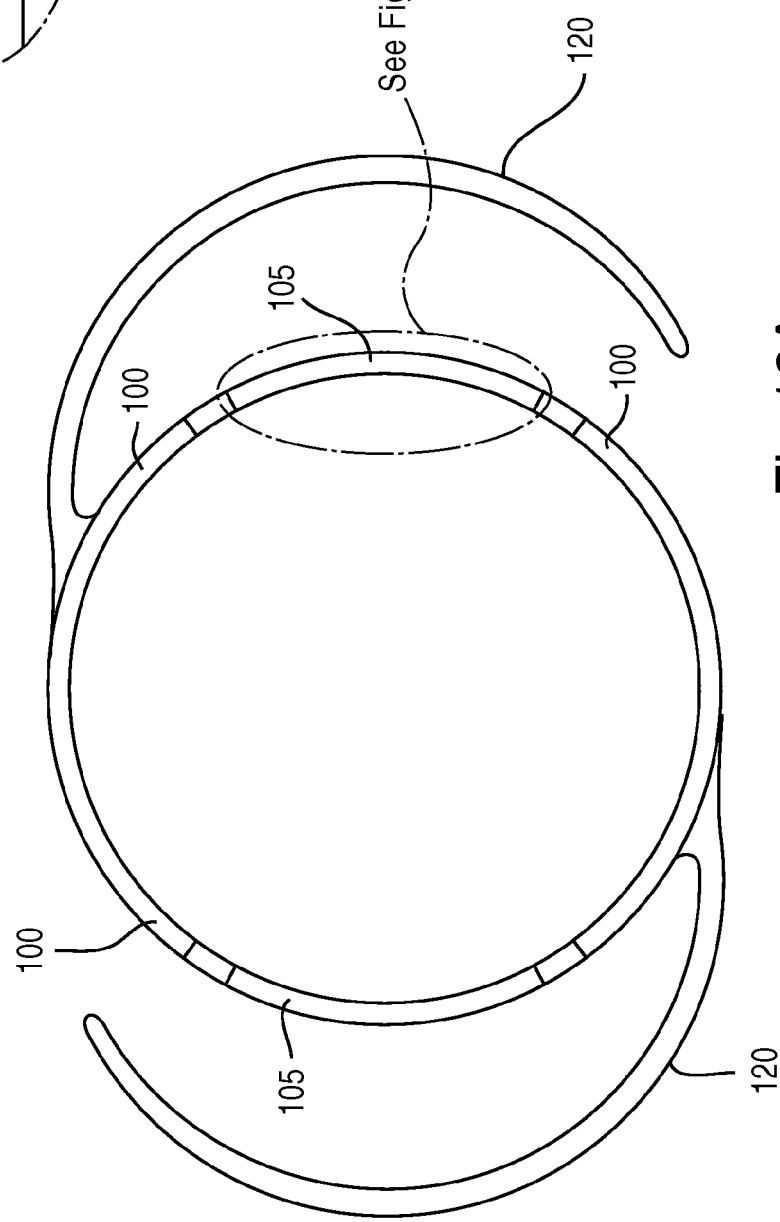
FIG. 12A is a top view of a base component of a currently known foldable multi-component intraocular lens.
Figure 13:
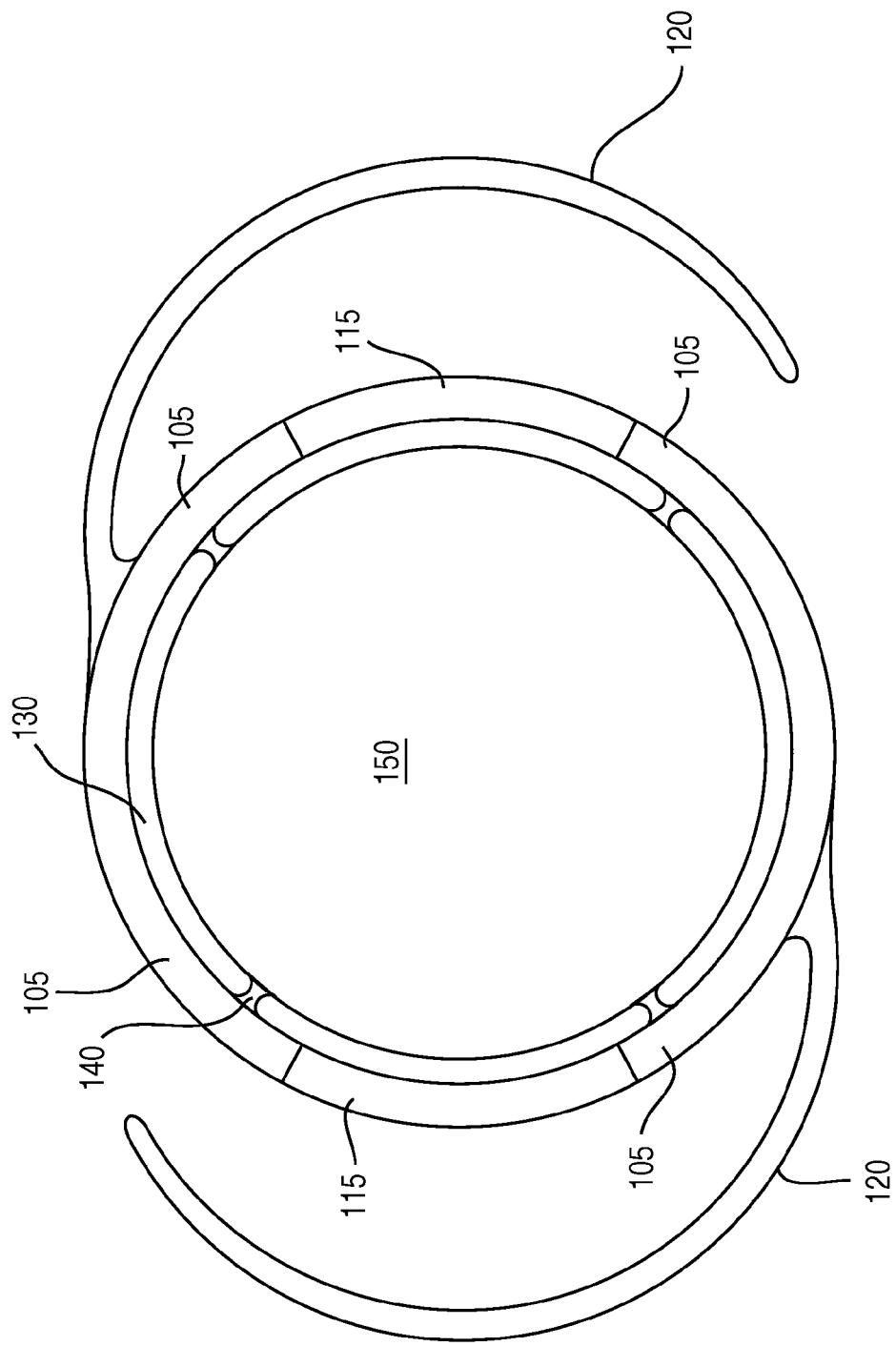
FIG. 13 is a top view of a base component of another currently known foldable multi-component intraocular lens.
Figure 15:
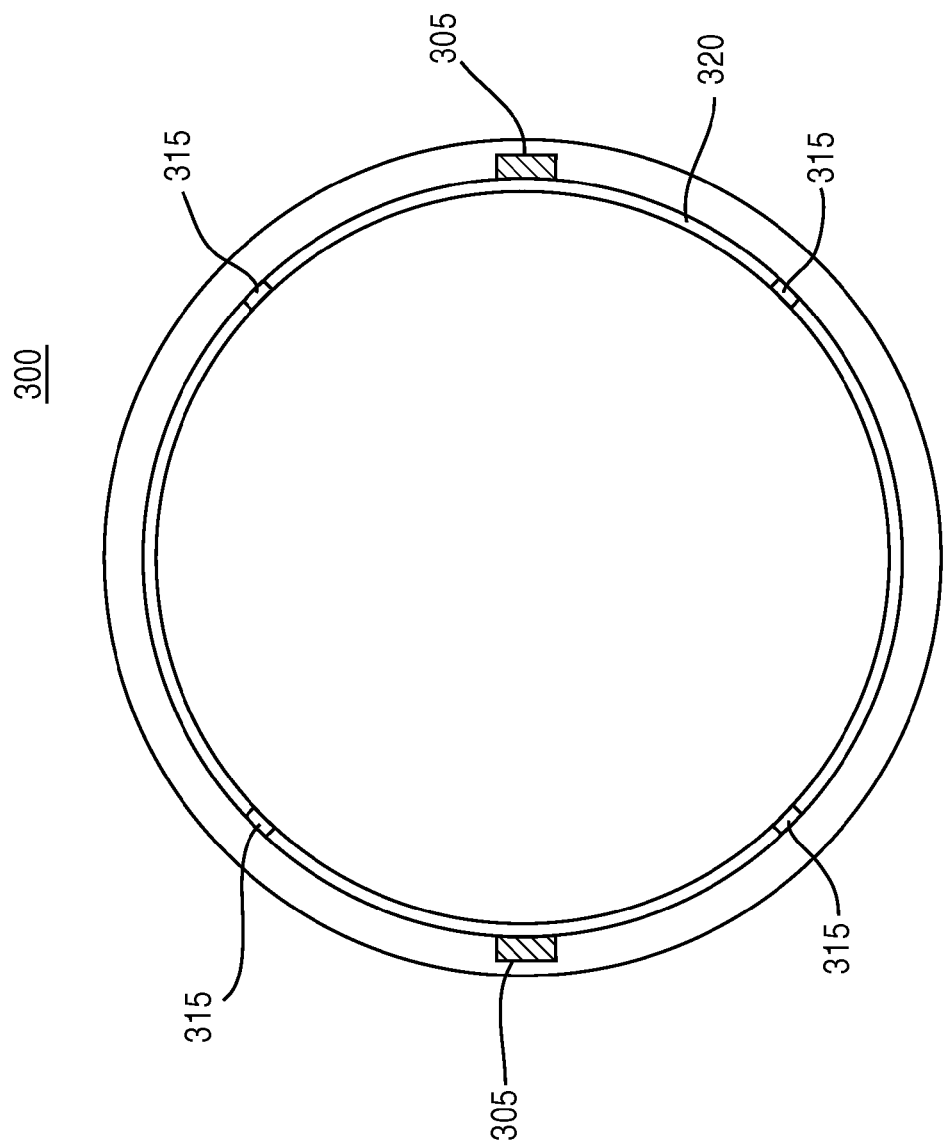
FIG. 15 is an exploded top view of the top lens component of a currently known foldable multi-component intraocular lens.
Figure 18:
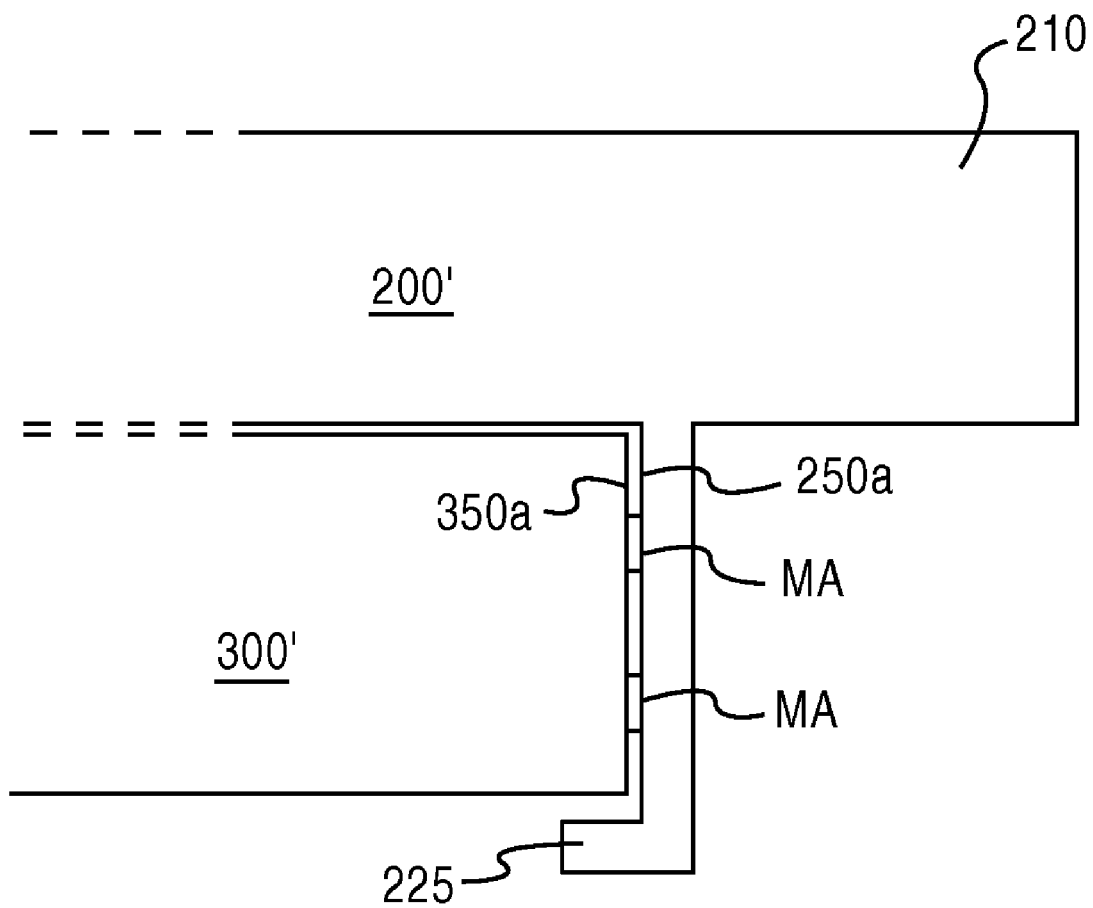
FIG. 18 is a side view of a currently known optical assembly wherein a mid lens engages a top lens.
Figure 19:
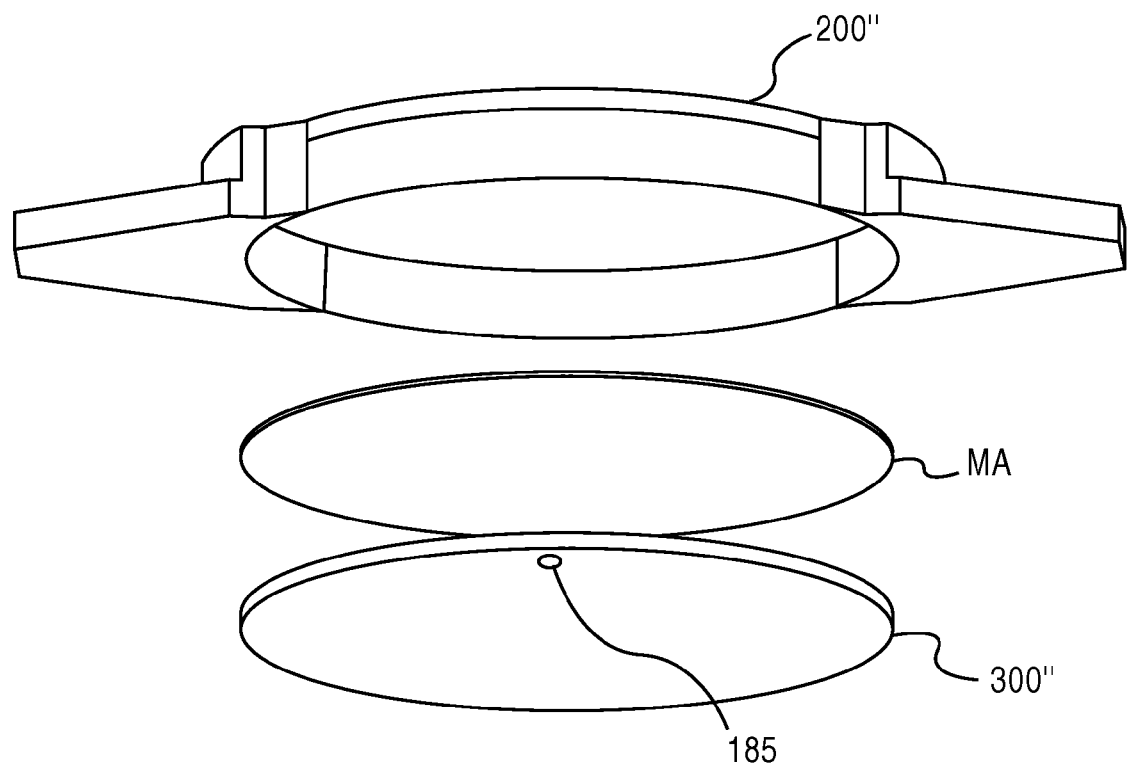
FIG. 19 is an exploded view of a currently known optical assembly.
Figure 20:
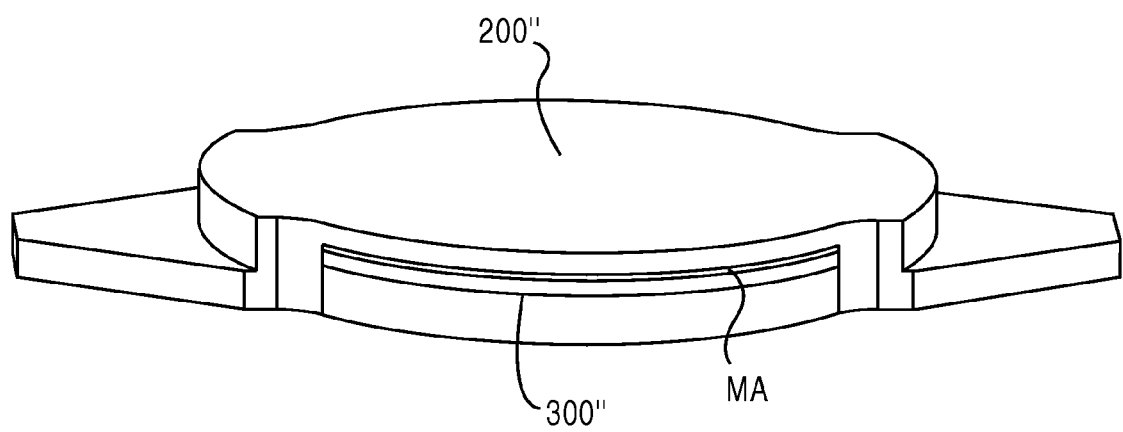
FIG. 20 is a perspective view of the optical assembly shown in FIG. 19 in the assembled state.
Figure 21:
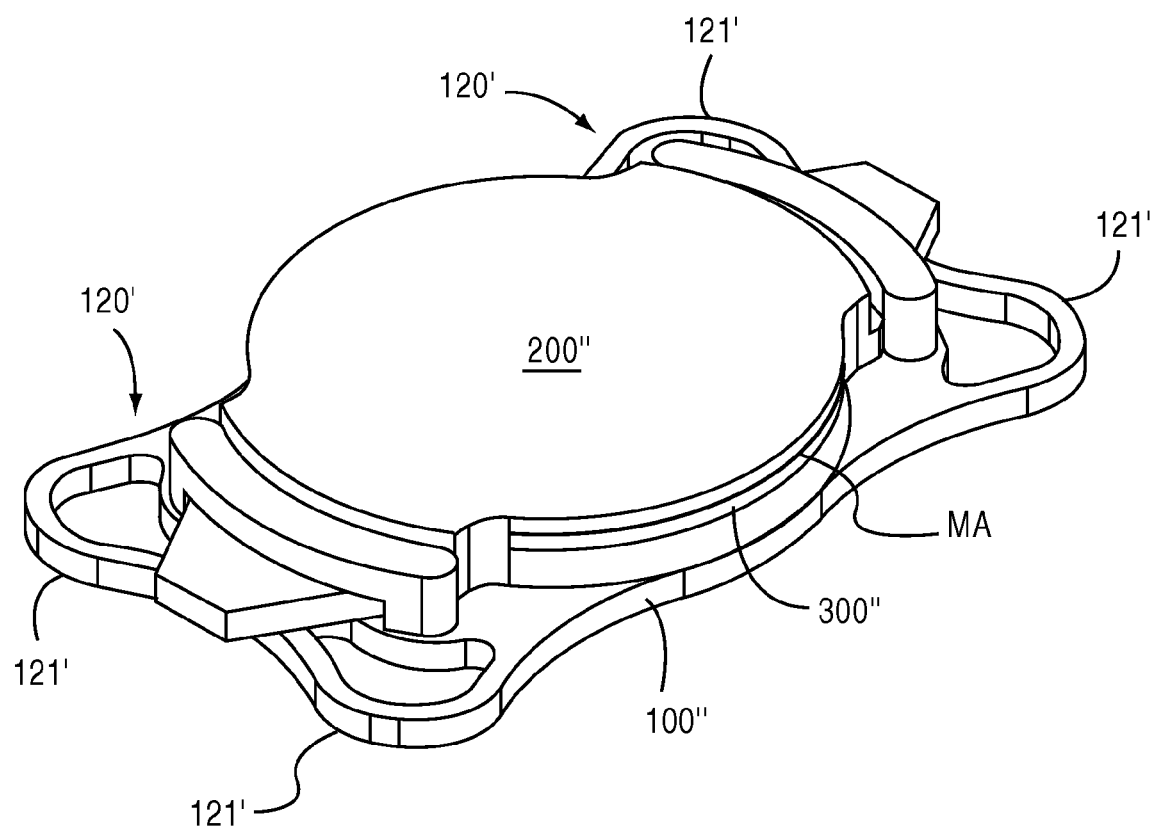
FIG. 21 is a perspective view of the optical assembly shown in FIG. 20 assembled with a base lens.
Figure 22:
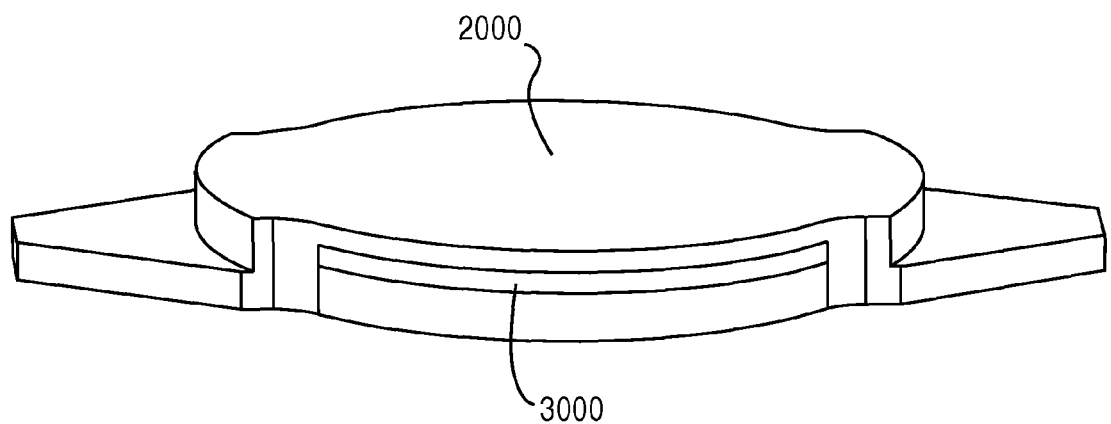
FIG. 22 is a perspective view of an optical assembly wherein a top lens and a mid lens are adhered to each other without the use of an adhesive provided therebetween according to an embodiment of the present invention.
Figure 23:
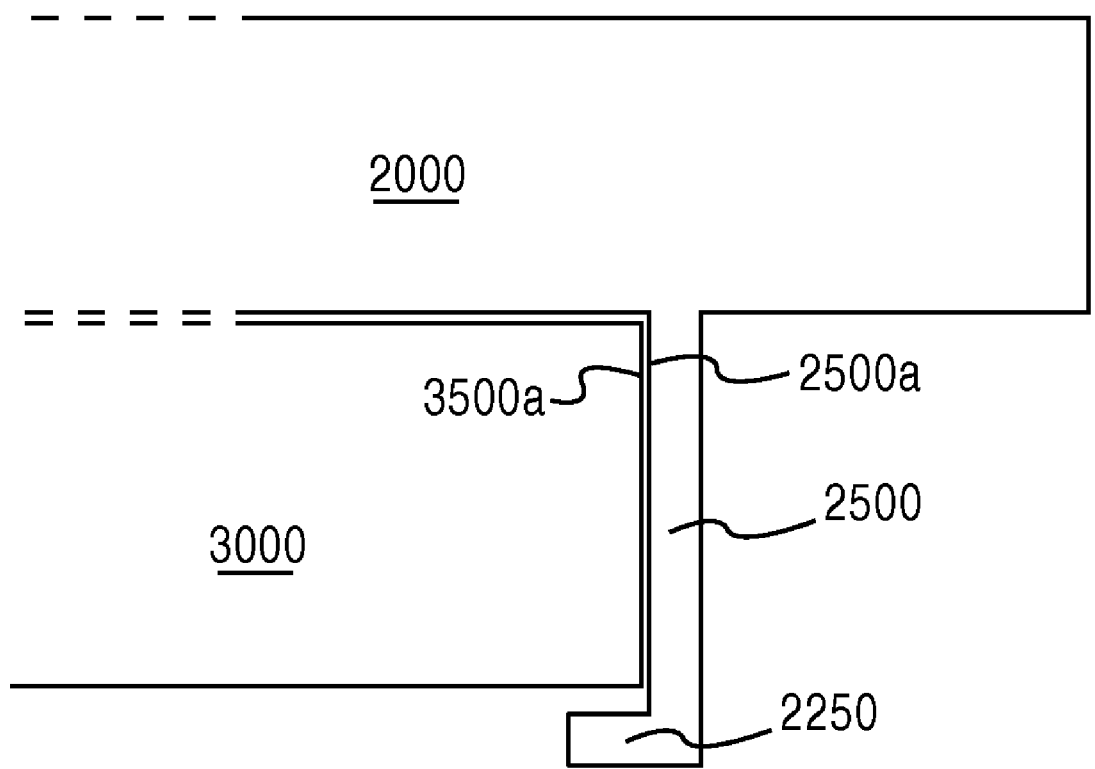
FIG. 23 is a side view of the optical assembly shown in FIG. 22, illustrating a region where the mid lens engages the top lens.

For example, a certain distinguishing aspect of the present invention relative to the disclosure of the '875 and '364 applications is the material from which the top lens 3000 and the mid lens 2000 are manufactured. In the present invention, the mid lens 2000 and top lens 3000 are manufactured from a preferably foldable material, e.g., hydrophilic acrylic, hydrophobic acrylic, silicone and the like, such that the mid and top lenses 2000 and 3000 inherently or naturally adhere or stick to each other such that the adhesive MA of the '364 application is not necessary, as is seen with hydrophilic acrylics. That is, as shown in FIG. 22, the top lens 3000 and mid lens 2000 adhere to each other without any of the adhesive MA from the '364 application disposed between opposing faces of the lenses 2000 and 3000, or between an outer peripheral surface 3500a of the top lens 3000 and an inner peripheral surface 2500a of a side portion 2500 of the mid lens 2000, as shown in FIG. 23.

While the top lens 3000 and mid lens 2000 are preferably manufactured from a hydrophilic material, it may not be necessary for the lenses 2000 and 3000 to be manufactured from the same hydrophilic material. For example, if the lenses 2000 and 3000 are manufactured from a hydrophilic acrylic material, a hydrophobic acrylic or any other suitable material, it may be that the natural physical and/or chemical properties of the material is such that the properties hold the lenses 2000 and 3000 together wherever the lenses 2000 and 3000 contact each other. Accordingly, the lenses 2000 and 3000 are very difficult to separate from each other. As such, the adhesive MA from the '364 application is omitted from the present invention, wherein assembly of the optical assembly including the top lens 3000 and mid lens 2000 is simplified, faster, needs less materials, and reduces the overall costs.

Figure 24:
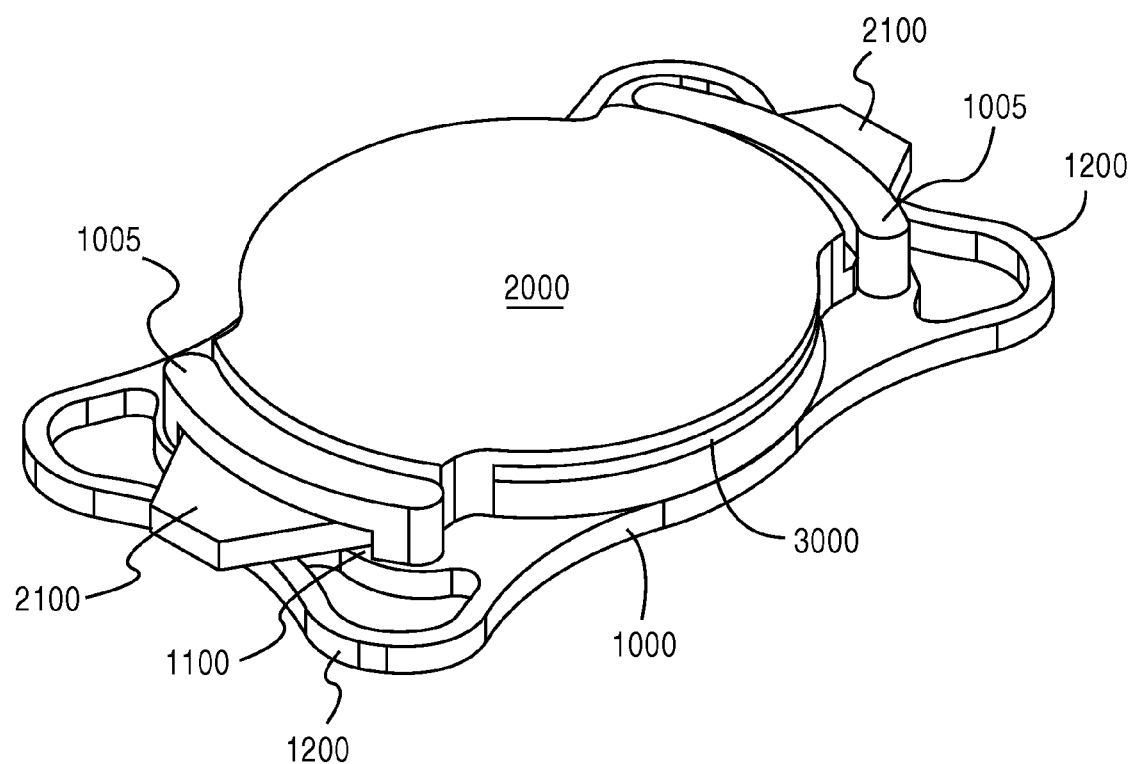
FIG. 24 is a perspective view of the optical assembly shown in FIG. 22 assembled with a base lens.

As shown in FIG. 24, which is an exemplary illustration of another aspect of the present invention in the assembled state, the optical assembly, i.e., the top lens 3000 and mid lens 2000, is first assembled by the lenses 2000 and 3000 being adhered together by the manufacturer. Then, at least one, and preferably two, projections 2100 of the mid lens 2000 portion of the optical assembly are passed through a corresponding slot 1100 defined in a corresponding flange 1005 of the base lens 1000 and overlaps a portion of the corresponding haptic 1200 of the base lens 1000.

According to the present invention, since the optical assembly, i.e., top lens 3000 and mid lens 2000, is exchangeable with another optical assembly in order to adapt or adjust the optical properties of the patient's vision, it is preferable that the optical assembly not be capable of adhering to any portion of the base lens 1000. In other words, the non-optical portions of the optical assembly, which includes portions of the optical assembly that physically contact or overlap with the base lens 1000, should be treated so as not to have any adhesive characteristics. That is, the non-optical portions of the optical assembly cannot adhere or otherwise stick to the base lens 1000 such that the optical assembly is prevented from being removed from the base lens 1000.

Figure 25:
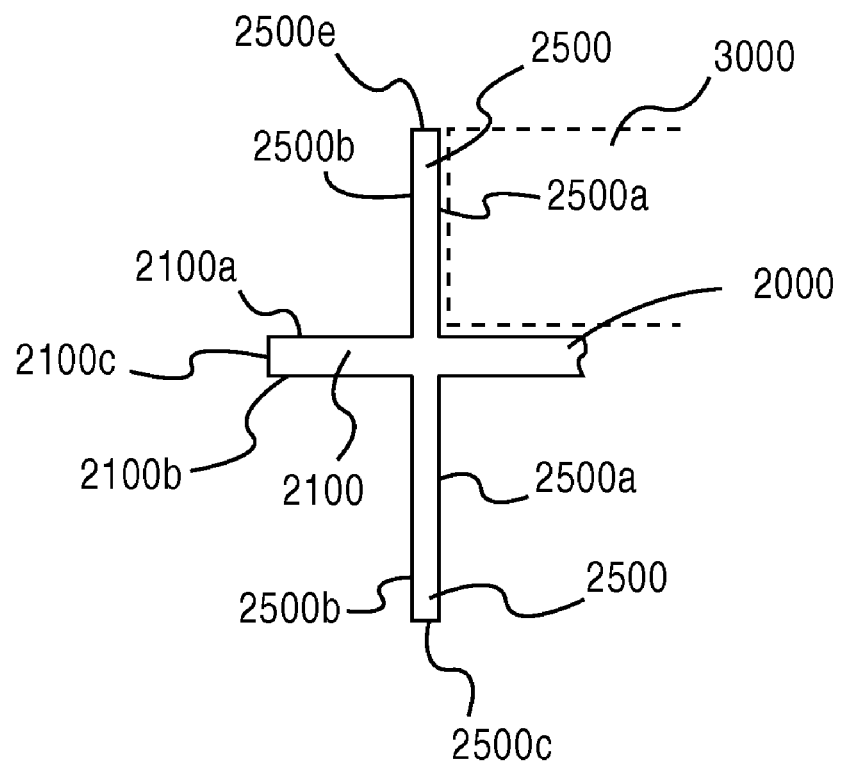
FIG. 25 is an exploded side view of a top lens illustrating regions that can be treated to have non-adhesive properties.

FIG. 25 is a schematic diagram of a portion of the mid lens 2000 which engages the top lens 3000 and also passes through or otherwise contacts the base lens 1000. The top lens 3000 is illustrated in dashed lines as abutting against the inner surface 2500a of an upper side portion 2500 of the mid lens 2000. That is, the top lens 3000 is shown, for exemplary purposes, as being placed on a top or upper surface thereof, however, it is also within the scope of the present invention for the top lens 3000 to be positioned on a lower surface of the mid lens 2000 so as to be abutting against the inner surface 2500a of a lower side portion 2500 thereof.

As such, it is possible for portions of the base lens 1000 to contact an outer surface 2500b of the side portion 2500, an upper surface 2500c of the side portion 2500, an upper surface 2100a of the projection 2100, a lower surface 2100b of the projection, and an outer surface 2100c of the projection 2100.

The possible contact surfaces 2500b, 2500c, 2100a, 2100b, and 2100c are subjected to a treatment that prevents such surfaces from being able to adhere to a corresponding portion of the base lens 1000 contacted by the surfaces.

Figure 26A:
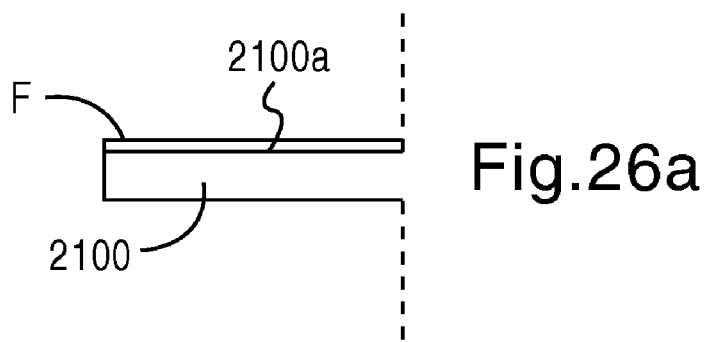
FIGS. 26A and 26B are schematic diagrams illustrating examples of how the regions illustrated in FIG. 25 can be treated.
Figure 26B:
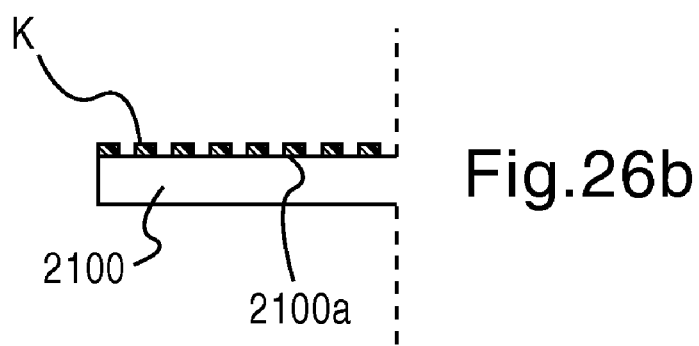

For example, at least one of the surfaces 2500b, 2500c, 2100a, 2100b, and 2100c can be frosted or otherwise chemically treated, or physically worked so as not to have any adhesive properties. For illustrative purposes, as shown in FIG. 26a, the upper surface 2100a of the projection 2100 is frosted F with a suitable chemical or substance that prevents the mid lens 2000 from being able to adhere to the base lens 1000. Alternatively, as shown in FIG. 26b, the upper surface 2100a of the projection 2100 is roughened or knurled to have a knurled surface K.

The actual surface that is treated will be determined by the embodiment or version of the lens and which portions of the optical assembly actually contact or overlap the base lens 1000. Accordingly, as stated above, the treated surface can be any one of or any combination of the various surfaces 2500b, 2500c, 2100a, 2100b, and 2100c and how the surface or surfaces 2500b, 2500c, 2100a, 2100b, and 2100c are treated can vary. Furthermore, although a knurled surface K is shown in FIG. 26b, it is within the scope of the present invention for the relevant surface 2500b, 2500c, 2100a, 2100b, and 2100c to be treated in any suitable manner, such as, but in no way intended to limit possible alternatives, shot peening, or coated with a non-adhesive polymer, and the like.

Moreover, as noted previously above, the mid lens 2000 and base lens 1000 may be made from different materials or at least materials that are not adhesive relative to each other.

While not illustrated, it should be noted that portions of the mid lens 2000 or other portions of the top lens 3000 that physically contact any portion of the base lens 1000 are also contemplated as being treated so as not to have any properties of portions that are able to adhere to the base lens 1000.

Therefore, the surfaces that can be treated are not limited to the outer portions of the optical assembly, but may also include the outermost planar surface of either lens 2000 or 3000, depending on whichever lens is contacting a corresponding planar surface of the base lens 1000. As such, by subjecting the possible contact surfaces 2500b, 2500c, 2100a, 2100b, and 2100c to a treatment that prevents such surfaces from being able to adhere to a corresponding portion of the base lens 1000 contacted by the surfaces, exchanging an existing optical assembly with a new optical assembly can be accomplishes easily and quickly, and without damaging aspects of the base lens 1000.

FIGS. 27A-D illustrate another aspect of the present invention. Previously, the optical assembly was described as having two optical elements, that is, the top lens 3000 and the mid lens 2000, adhered together. Preferably, the top lens 3000 would be a toric lens (cylindrical, non-spherical) and the mid lens 2000 would be a non-toric lens (spherical, multi-focal). According to the present invention, the optical assembly may include additional optical elements wherein the top lens 3000, mid lens 2000, and any additional lens 4000 would be provided in a stacked arrangement within the optical assembly. It should be noted that although FIGS. 27A-C illustrate three optical elements (i.e., lenses 2000, 3000 and 4000), it is within the scope of the invention for additional lenses to be included such that there are four, five, six, . . . twelve lenses provided in a stacked arrangement within the optical assembly. However, four lenses are discussed herein to simplify the understanding thereof.

For example, as shown in FIG. 27A, if the top lens 3000 is a toric (non-spherical) lens and the mid lens 2000 is a non-toric lens (spherical), then the additional lens 4000, which in the illustrated example is provided between the mid lens 2000 and base lens 1000, may add chromophores or address different types of optical aberration. It should be understood that the lenses 2000, 3000, and 4000 are manufactured from a material having the adhesive properties such that the lenses 2000, 3000 and 4000 are inherently held together by their natural physical and/or chemical properties. The lenses 2000, 3000 and 4000 can further be held together by a flange 225 extending radially inward from an upper end of the side portion 2500. See FIG. 16 for an example of the flange 225.

Also, it is within the scope of the present invention to adjust or alter the order in which the lenses 2000, 3000 and 4000 are arranged in the optical assembly. For example, as shown in FIG. 27B, the top lens 3000 and mid lens 2000 may be switched such that the additional lens 4000 is provided between the base lens 1000 and the top lens 3000. Furthermore, for example only, the additional lens 4000 can be positioned furthest from the base lens 1000, as shown in FIG. 27C.

The order in which the lenses are arranged in the optical assembly can be changed to suit the desired optical properties to be obtained by the optical assembly. Furthermore, the type of optical correction provided by each lens, e.g., spherical, toric, chromophore, astigmatism, night vision, and the like, of the optical assembly may vary depending on the optical properties needed by the patient.

For example, as shown in FIG. 27D, an exemplary embodiment is illustrated wherein the mid lens 2000 is positioned between the base lens 1000 and the top lens 3000 as described above. Further, the additional lens 4000 can be a lens that corrects or addresses a spherical aberration and is positioned between the mid lens 2000 and the base lens 1000, wherein yet other lenses 5000, 6000, 7000 and 8000 are positioned between the mid lens 2000 and the base lens 1000, and wherein the lens 5000 can correct or address higher order aberrations, lens 6000 can be a multi-focal lens, lens 7000 can be an aspheric lens, and lens 8000 can be a chromofore lens. It should be noted that the types of optical conditions that the additional lenses 4000 through 7000 correct or address, as well as their location or arrangement within the optical assembly, described above is merely exemplary and it is intended that the optical conditions corrected or addressed by each lens, and the location of each lens within the optical assembly may vary as needed to provide the desired optical properties. For example, it is within the scope of the invention for the mid lens 2000 to be provided between the base lens 1000 and the top lens 3000, wherein some of the lenses 4000, 5000 and 6000 can be provided between the base lens 1000 and the mid lens 2000, while the other lens 7000 or lenses can be provided between the mid lens 2000 and the top lens 3000. Of course, the location of the mid lens 2000 and top lens 3000 can be switched and the location of the other lenses 4000, 5000, 6000, and 7000, for example, can also be rearranged based on the needed optical properties to be provided by the optical assembly.

Furthermore, it should be noted that it is within the scope of the present invention for a space to be located between lenses. For example, referring to FIG. 27D, any one of the reference numbers, e.g., 4000, 5000, 6000 and 7000, could represent or illustrate a space or gap between neighboring lenses. In other words, it is envisioned that reference number 6000 would not be a lens, but instead defines a space or gap between lenses 5000 and 7000. Similarly, but in no way limiting the scope of the invention, reference numbers 5000 and 7000 could define a space or a gap between base lens 1000 and lens 6000, and lens 6000 and lens 4000. It is within the scope of the invention for there to be no gap between lenses, a single gap defined between neighboring lenses, a plurality of gaps or spaces defined between neighboring lenses within the optical assembly, as well as any number of permutations of the spaces or gaps relative to the neighboring lenses.

Also, it is within the scope of the invention for a chamber to be defined between neighboring lenses, wherein the chamber would hold or contain a liquid, or semi-solid, or a gelatinous material having pharmalogical and/or optical properties.

It is also within the scope of the present invention for the base lens 1000 to be a spherical lens or an aspherical lens, depending on the desired optical properties to be provided by the inventive optical assembly to the patient.

In yet another embodiment of the present invention that is illustrated in FIG. 28, the mid lens 2000 and top lens 3000 have, until now, been described as separate and distinct components of the optical assembly. However, it is also within the scope of the present invention to combine the mid lens 2000 and top lens 3000 to form an integrated, single lens 8000 that engages the base lens 1000 to form the optical assembly. For example, a bottom surface of the lens 8000, that is, the half of the lens 8000b closest to the base lens 1000, can be or define a non-toric surface, while a top surface of the lens 8000a furthest from the base lens 1000, can be or define a toric surface. The optical properties of the sections of the lens 8000a and 8000b can be formed by lathing or molding the surfaces to produce the toric, non-toric, multifocal, etc. optical properties. The surgeon further customizes the lens 8000 by it's surgical orientation in the eye, which is determined by the surgeon at the time of the primary surgery. Alternatively, the surgeon can use a fully customized front lens assembly 2000, 3000, 4000, 5000, 6000, 7000, where the orientation is set by the manufacturer as specified by the surgeon (fully customized manufacturing). Here, the surgical orientation would always be the same.

It is also within the scope of the present invention for the optical assembly having the base lens, mid lens and top lens, for example, to be preassembled by the surgeon prior to the surgical procedure. The entire optical assembly can then be injected into the eye of the patient, rather than individual components being inserted one at a time by the surgeon.

Sometimes, while the eye is healing after a surgical procedure during which an intraocular lens system is implanted in the eye, the top lens of the intraocular lens system rotates. To determine if the lens has rotated, it is also within the scope of the present invention for a fluorescent dye or some other material or chemical that is not visible in natural light by the human eye to be incorporated into the top lens by the manufacturer prior to surgical use and function as an orientation mark, much like the mark 85 illustrated in FIG. 5A. The location of the mark 85 may vary from a mark on the outer peripheral edge of the top lens to a line spanning across the entire or partial central portion of the lens. If such a rotation were to occur, the front lens assembly (mid lens 2000, top lens 3000, etc.) would be removed and exchanged with a new custom front lens assembly provided by the manufacturer according to the surgeon's post operative measurements. After the primary surgery, the orientation of the base lens and therefore the front lens assembly as well is fixed by virtue of the capsule contracture around the haptics. Therefore, in any secondary enhancement operation, any orientation and/or axis configuration must be customized by the manufacturer according to the surgeon's postoperative measurements. This is in contrast to the primary surgery where either the surgeon does have the ability to determine orientation as an alternative option to the manufacturer doing this in a fully customized front lens. The exchange of the front lens assembly can occur at any time in the patient's life after the primary surgery and for any reason, i.e., unintended postoperative rotation of the lens, dissatisfaction on the part of the patient because of optic distortion seen with some multifocal optics, changes of medical condition of the eye, e.g., SMD, etc.

As such, the present invention may provide a relatively simple, easy to manufacture and insert intraocular lens implant that provides the patient with a customized optical assembly configured to address the particular needs of the patient's vision.

While the invention has been described in conjunction with regards to specific embodiments, it is evident that various changes and modifications may be made, and the equivalents substituted for elements thereof without departing from the true scope of the invention. In addition, many modifications may be made to adapt a particular situation or material to the teachings of the invention without departing from the scope thereof. Therefore, it is intended that this invention not be limited to the particular embodiments disclosed herein, but will include all embodiments within the spirit and scope of the disclosure.

What is claimed is:

1. A multi-component intraocular lens implantable in an optical system of a human eye, comprising:
   a base lens having an anterior surface configured to face a front of the human eye, a posterior surface on an opposite side of the base lens relative to the anterior surface and configured to face a back of the human eye, a circumferential side surface connecting the anterior and posterior surfaces, and being manufactured from a base foldable material, the base lens including at least one notch defined in the circumferential side surface of the base lens and a flange configured to engage the notch; and
   an optical assembly including a first lens and a second lens, the first and second lenses being manufactured from first and second foldable materials, respectively, wherein the first lens adheres directly to the second lens free of any material or substance present therebetween,
   wherein the flange is disposed on and extends orthogonally away from the anterior surface of the base lens toward the front of the human eye, the flange includes a slot defined therein and through which the base lens selectively engages the optical assembly, the slot being located only above the anterior surface of the base lens.

2. The intraocular lens of claim 1, wherein the second foldable material includes one of a hydrophilic acrylic and a hydrophobic acrylic.

3. The intraocular lens of claim 1, further comprising at least one axis orientation mark provided thereon.

4. The intraocular lens of claim 3, wherein the intraocular lens is configured to rotate within the human eye relative to the at least one axis orientation mark.

5. The intraocular lens of claim 1, wherein the first lens is a mid lens and the second lens is a top lens.

6. The intraocular lens of claim 5, wherein either the mid lens is disposed between the top lens and the base lens or the top lens is disposed between the mid lens and the base lens.

7. The intraocular lens of claim 5, wherein the mid lens comprises at least one projection extending away from an outer circumferential surface of the mid lens and which is configured to engage the slot defined in the flange of the base lens.

8. The intraocular lens of claim 7, wherein an exposed surface of at least one of the at least one projection and the outer circumferential surface of the mid lens includes a non-adhesive region.

9. The intraocular lens of claim 8, wherein the non-adhesive region is one of frosted, a non-adhesive polymer coating, knurled and shot-peened.

10. The intraocular lens of claim 7, wherein the at least one projection includes two projections, a first projection extending in a first direction and a second projection extending in a second direction that is different from the first direction.

11. The intraocular lens of claim 10, wherein a contact surface of the optical assembly which contacts the posterior surface of the base lens includes a non-adhesive region.

12. The intraocular lens of claim 11, wherein the non-adhesive region is one of frosted, a non-adhesive polymer coating, knurled and shot-peened.

13. The intraocular lens of claim 1, wherein the optical assembly further comprises at least one additional lens manufactured from an additional foldable material.

14. The intraocular lens of claim 13, wherein the at least one additional lens is provided between the first lens and the base lens and adheres only to the first lens.

15. The intraocular lens of claim 14, wherein the at least one additional lens comprises a third lens and a fourth lens.

16. The intraocular lens of claim 13, wherein the second lens is provided between the first lens and the base lens, and the at least one additional lens is provided between the second lens and the base lens and adheres only to the second lens.

17. The intraocular lens of claim 16, wherein the at least one additional lens comprises a third lens and a fourth lens, the third lens adheres to the fourth lens and to the second lens.

18. The intraocular lens of claim 13, wherein the at least one additional lens is provided between the first and second lenses and adheres to both the first and second lenses.

19. The intraocular lens of claim 18, wherein the at least one additional lens comprises a third lens and a fourth lens.

20. The intraocular lens of claim 13, wherein the at least one additional lens is provided on an anterior surface of either one of the first and second lenses, wherein the first and second lenses are disposed between the at least one additional lens and the base lens, and the at least one additional lens adheres to whichever of the first and second lens is most remote from the base lens.

21. The intraocular lens of claim 20, wherein the at least one additional lens comprises a third lens and a fourth lens.

22. The intraocular lens of claim 13, wherein the at least one additional lens comprises a third lens and a fourth lens, the third lens being provided between the first lens and the base lens and adhering only to the first lens, and the fourth lens being provided between the first lens and the second lens and adhering to both the first and second lenses.

23. The intraocular lens of claim 13, wherein the first lens, the second lens and the at least one additional lens each have different optical properties relative to each other.

24. The intraocular lens of claim 23, wherein the different optical properties are selected from the group consisting of toric, non-toric, spherical aberrations, higher order aberrations, multi-focal, aspheric, and chromofore.

25. The intraocular lens of claim 13, wherein a chamber is defined between one of the first lens and the second lens of the optical assembly and one of the at least one additional lens of the optical assembly and the base lens.

26. The intraocular lens of claim 1, wherein the base lens is one of spherical and aspherical.

27. The intraocular lens of claim 1, wherein a chamber is defined between one of the first lens and the second lens of the optical assembly and the base lens.

28. A multi-component intraocular lens implantable in an optical system of a human eye, comprising:

a base lens having an anterior surface configured to face a front of the human eye, a posterior surface on an opposite side of the base lens relative to the anterior surface and configured to face a back of the human eye, a circumferential side surface connecting the anterior and posterior surfaces, and being manufactured from a base foldable material, the base lens including at least one notch defined in the circumferential side surface of the base lens and a flange configured to engage the notch; and an optical assembly including a first lens and a second lens, the first and second lenses being manufactured from first and second foldable materials, respectively, wherein the first lens and the second lens are integrated to form a single lens, wherein the flange is disposed on and extends orthogonally away from the anterior surface of the base lens toward the front of the human eye, the flange includes a slot defined therein and through which the base lens selectively engages the optical assembly, the slot being located only above the anterior surface of the base lens.

* * * * *